US010201304B2

United States Patent
Vardy

(10) Patent No.: US 10,201,304 B2
(45) Date of Patent: Feb. 12, 2019

(54) MEASUREMENT OF PHYSIOLOGICAL CHARACTERISTICS

(71) Applicant: Terence Vardy, Tweed Heads (AU)

(72) Inventor: Terence Vardy, Tweed Heads (AU)

(73) Assignee: IsoTechnology Pty Ltd, Burleigh Waters, Queensland (AU)

( * ) Notice: Subject to any disclaimer, the term of this patent is extended or adjusted under 35 U.S.C. 154(b) by 372 days.

(21) Appl. No.: 14/776,809

(22) PCT Filed: Mar. 20, 2014

(86) PCT No.: PCT/AU2014/000298
§ 371 (c)(1),
(2) Date: Sep. 15, 2015

(87) PCT Pub. No.: WO2014/146174
PCT Pub. Date: Sep. 25, 2014

(65) Prior Publication Data
US 2016/0022195 A1 Jan. 28, 2016

(30) Foreign Application Priority Data

Mar. 20, 2013 (AU) .................. 2013201734

(51) Int. Cl.
*A61B 5/00* (2006.01)
*A61B 5/0295* (2006.01)
(Continued)

(52) U.S. Cl.
CPC ............ *A61B 5/4064* (2013.01); *A61B 5/026* (2013.01); *A61B 5/0295* (2013.01);
(Continued)

(58) Field of Classification Search
CPC ....... A61B 5/4064; A61B 5/026; A61B 5/742; A61B 5/7235; A61B 5/6814; A61B 5/0537; A61B 5/0295
See application file for complete search history.

(56) References Cited

U.S. PATENT DOCUMENTS 8,277,385 B2 * 10/2012 Berka ................ A61B 5/02433
600/485
2005/0177062 A1 8/2005 Skrabal et al.
(Continued)

FOREIGN PATENT DOCUMENTS

WO 2003/003920 A2 1/2003
WO 2004/047635 A1 6/2004
(Continued)

OTHER PUBLICATIONS

International Search Report and Written Opinion of the International Searching Authorirty for PCT/AU2014/000298, dated Jun. 17, 2014 (Jun. 17, 2014).
(Continued)

*Primary Examiner* — Tiffany Weston
*Assistant Examiner* — Tho Tran
(74) *Attorney, Agent, or Firm* — Bradley Arant Boult Cummings LLP

(57) ABSTRACT

A system for measuring physiological aspects has a non-invasive monitor configured to generate monitor signals relating to fluid characteristics in the head and body. A computational device is operatively connected to the monitor and is configured to process the monitor signals to generate characterizing data relating to at least one of regional fluid volumes, intra/extracellular fluid volume ratios and blood flow. A data output device is connected to the computational device and is configured to output the characterizing data. A method and a computer program
(Continued)

product for recording, measuring, and displaying physiological characteristics are also provided.

15 Claims, 22 Drawing Sheets

(51) Int. Cl.
    *A61B 5/053*     (2006.01)
    *A61B 5/026*     (2006.01)

(52) U.S. Cl.
    CPC .......... *A61B 5/0537* (2013.01); *A61B 5/6814* (2013.01); *A61B 5/7235* (2013.01); *A61B 5/742* (2013.01)

(56) References Cited

U.S. PATENT DOCUMENTS

2008/0027342 A1* 1/2008 Rouw ................ A61B 5/04085
    600/513
2009/0264776 A1   10/2009  Vardy
2011/0196245 A1*  8/2011  Poupko .............. A61B 5/02028
    600/506

FOREIGN PATENT DOCUMENTS

WO     2005/010640 A2     2/2005
WO     2013/153454 A2     10/2013

OTHER PUBLICATIONS

Moskalenko Y, et al., Multifrequency REG: Fundamental Background, Informational Meaning and Ways of Data Analysis and Automation. American Journal of Biomedical Engineering, 2(4) pp. 163-174, 2012. paragraphs 37, 55, 3, 64,190.

Moskalenko Y, et al., Changes of Circulatory-Metabolic Indices and Skull Biomechanics with Brain Activity during Ageing. Journal of Integrative Neuroscience, vol. 10, No. 2 (2011) pp. 131-160. Paragraph 2.5 and Figure 1.

* cited by examiner

FIGURE 20

MEASUREMENT OF PHYSIOLOGICAL CHARACTERISTICS

CLAIM FOR PRIORITY

This application claims priority under 35 USC 371 to International Application No. PCT/AU2014/000298, filed on Mar. 20, 2014, which claims priority to Australian Patent Application No. 2013201734, which was filed on Mar. 20, 2013, each of which is hereby incorporated by reference in its entirety.

FIELD OF THE INVENTION

The present invention generally relates to the measurement of physiological characteristics. In particular, the present invention generally relates to a method, a system and a software product to measure and display the dielectric properties of the fluid mediums within the head and body of humans and animals.

BACKGROUND ART

[Mere reference to background art herein should not be construed as an admission that such art constitutes common general knowledge in relation to the invention.]

Redistributions of fluids between segments of the head and body are often of central clinical importance, particularly in humans. This includes redistributions of fluids between the intra-cellular and extra-cellular compartments within the segments. Measurement of these redistributions can be useful, particularly for monitoring and assessing the response and adaptation of the body to various orthostatic and anti-orthostatic dysfunctions.

However, currently employed methods of measuring redistributions of fluids between segments of a body are either invasive or bulky and expensive. For example, tracer dilution techniques involve invasively administering a dose of an appropriate tracer to the body, collecting blood samples, and measuring the tracer. The tracer fluid does not always safely disperse after the test. Alternatively, MRI technologies can be used but MRI equipment is both costly and bulky, making, it impractical readily to measure redistributions of fluids between segments of a body. A further disadvantage of these techniques is that they do not yield easily used real-time data during physiological stress or clinical diagnosis. Nor are there auto-regulation or homoeostatic balance ranges that can be applied generally to both adults and infants. An elderly adult, mature adult, young adult, child, infant (male or female) may have different ranges of auto-regulation.

The amount of "water" that a cell takes on in the brain is of critical, importance in brain injury management as is the cardiovascular competence level of the heart/lung/body.

The individual should be able to maintain body "homeostasis"—when the person cannot "Auto-regulate" then he/she has exceeded reasonable physiologic capacity.

SUMMARY OF THE INVENTION

According to a first aspect of the invention, there is provided a system for measuring physiological characteristics, the system comprising:

a non-invasive monitor configured to generate monitor signals relating to fluid characteristics of the body;

a computational device operatively connected to the monitor and configured to process the monitor signals to generate characterising data relating to at least one of the regional fluid volumes, intra/extracellular fluid volume ratios and blood flow; and a software program installed on the computational device and configured to record, calculate, and display the characterising data.

The generated characterising data may be in the form of any one or more of the following which are also capable of being displayed in various formats:

1. CCe (Cranial Compliance)
2. CSFm (Cerebrospinal fluid movement)
3. CBF (Cerebral blood flow)
4. CVR (Cardio Vascular Reactivity)
5. R1 (extracellular resistance)
6. R2 (intracellular resistance)
7. C (brain tissue capacitance)
8. ReZ (full brain tissue resistance)
9. The ratio of reactance and resistance tgφ=ImZ/ReZ—the phase angle of brain bio-impedance.
10. Spectral Analysis The non-invasive monitor is preferably a multi-frequency multi-channel impedance rheoencephlagraph (REG) in conjunction with a Transcranial Doppler (TCD).

Specifically, the rheoencephalograph waveform combined with the Transcranial Doppler waveform produces a unique new waveform that allows for the generation of the characterising data. In particular, the rheoencephalograph can determine capacitance and resistance for different tissue structures and distinguish between connective tissue and blood. In other words, the rheoencephalograph can distinguish between intracellular fluid volume of one or more cells and extracellular fluid.

The system has the capacity to separately monitor the left hemisphere and the right hemisphere of the head as a portion of the body.

The software program installed on the computational device will preferably have capacity to record steady state resistance on each frequency as well as the pulsing wave on 3 frequencies. Additional frequencies may be necessary to provide even more specific monitoring capacity.

The steady state resistance values are preferably received at a frequency of 100 times per cardiac cycle.

The software program is preferably automated to perform the necessary calculations on this monitor signals and compute values for R1, R2 and C from the data contained in the monitor signal and plot the changes during any single selected cardiac cycle.

Measurements of basic resistance between electrodes of a preferred rheoencephalograph device are possible to calculate parameters associated with head tissue. From an electrical point of view, brain tissue may be represented as a set of resistances and capacities intricately connected to each other. Formulae can then be used to calculate the required parameters. Views of persons in the art differ as to the best equivalent circuit of the brain and the formula chosen typically depends upon which equivalent circuit of the brain is selected. Two different equivalent circuits of the brain are illustrated in FIGS. 26 and 27.

The equivalent electrical circuit of the brain represented in FIG. 26 provides Formula (1):

$$Z = \frac{R_1\left(R_2 + \frac{1}{i\omega C}\right)}{R_1 + R_2 + \frac{1}{i\omega C}}, \tag{1}$$

Where:
  Z is the brain tissue impedance;
  $R_1$ is the extracellular resistance;
  $R_2$ is the intracellular resistance;
  C is the cellular electric capacitance;
  ω is the angular frequency; and
  i is the imaginary unit $i=\sqrt{-1}$.

The equivalent electrical circuit of the brain represented in FIG. 22 provides Formula (2):

$$Z = \frac{(R_e + R_i) + i\omega CR_e R_i}{1 + i\omega CR_i}, \qquad (2)$$

Where:
  Z is the brain tissue impedance;
  $R_e$ is the extracranial resistance,
  $R_i$ is the intracranial resistance;
  C is the cellular electric capacitance; and
  ω is the angular frequency.

Future progress in this mode of calculation, which could permit additional data to be received, could be based on including one more frequencies, for example, any one or more of 16 kHz, 32 kHz, 50 kHz, 100 kHz, 150 kHz, 200 kHz or 250 kHz, in addition to or instead of the frequencies suggested in the preferred embodiment.

Estimation may be performed by interpolation methods. By having three measurements at three various frequencies the impedance function can be approximated with a simpler function Z(f). Thereafter, estimation of the impedance value at a fourth frequency with function Z(f) can be achieved by interpolation. The calculations as presented substantiate the conclusion that the transcephalic measurement of electrical impedance that has been used is a measurement of the electrical impedance of the whole head as the volume conductor from the head surface by a non-invasive method.

The program preferably allows computation automatically of values of impedance parameters ($R_1$, $R_2$, C in circuit—FIG. 32 and $R_e$, $R_i$, C in circuit FIG. 27).

Input data for the preferred software are values of impedance measured at three preferred distinct frequencies (16 kHz, 100 kHz, 200 kHz). The least squares method can be used to estimate the parameters of impedance magnitude. The impedance parameters are reduced to finding the minimum regression sum using the following formula:

$$S = \sum_{i=1}^{3} (|Z|_i - I_i)^2.$$

For solving the minimum of the regression sum, the quasi-Newton BGFS method is preferred and is typically included in the software.

These manipulations allow evaluation of different brain impedance parameters in each of the circuits.

The method of calculation of CSF mobility and CCe indexes is typically presented by special automation on the base of selecting of systolic and diastolic fragments (pre and post maximal value of the TCD pulse) and exporting this data to the software for display or output.

The first step is preferably normalization of data, which is the transformation of the real ranges of TCD and REG pulse changes to a scale with limits of 0.0-1.0. It is then possible to create an initial "XY" plot (plot 1), where X is Doppler and Y is REG (100 kHz). This plot may be approximated by a straight line (line 1). Coordinates of the first point in this line are (X1, Y1) and the last point are (X2; Y2). CCe value may be estimated as the negative tangent of the slope angle of this line.

$$CCe = |k| = -\tan\alpha = \left|\frac{y_2 - y_1}{x_2 - x_1}\right| \qquad (3)$$

where α is the slope angle of line 1.

Using this data, a new X',Y' plot (plot 2) is created from the second half of the pulse data, where X' is TCD and Y' is REG (100 kHz). Next, the area parameter of the new plot is estimated.

For this estimation, the plot is approximated by a straight line (line 2). The coordinates of the first point in this line are (X3; Y3) and the last points are (X4; Y4).

CSFm may then be estimated as the residual between the total (line 2) area and integral of (plot 2).

$$CSFm = \left(\frac{y_3 + y_4}{2}\right)*(x_4 - x_3) - \int_{x_1}^{x_2} f(x)dx \qquad (4)$$

where f(x) is the function of plot 2.

The software is preferably automated to perform the necessary calculations on the data and compute values for $R_1$, $R_2$ and C from this data and plot the changes during any single selected cardiac cycle.

According to a particularly preferred embodiment, there are two different ways of analysing multi-frequency data:

1. Calculations of $R_1$, $R_2$, C based on resistance values between electrodes with three different frequencies gives information about steady state conditions for comparison of different individuals or for the same individual with different physiological conditions—For example before and after brain surgery as well as evaluation of changes in brain tissue during the recovery period. For these purposes it is necessary to calculate these parameters every 5 seconds.

2. Calculations of changes of $R_1$, $R_2$, C during the cardiac cycle. $R_1$ represents the resistance of the skull bones and its connective tissues. If a value of $R_1$ is only occasionally sampled it will always be 'generally unchanging'. However if it is sampled 100 times per cardiac cycle the values will demonstrate a pulsating wave and should correspond to CCe or the elasticity of the skull bone interfaces during the cardiac cycle.

The software of one preferred embodiment also allows the calculation of spectral analysis.

The accuracy of the method can be (and has been) confirmed by comparing the resistance spectrum to the rheoencephalograph pulsing spectrum (i.e. slow fluctuations). R2/C=changing of intracranial fluids divided by the unchanging value of the brain tissue which corresponds to CSFm.

The rheoencephalograph is combined with dopplergraphy to produce a unique new waveform for input to the software and thus provide a completely new way to evaluate intracranial fluid dynamics. Additionally, it provides a basis for the meaning of CCe as essentially being a measurement of skull bone elasticity or movement between the skull bones at their connecting joint surfaces.

Based on the fact that the reactive component "C" (capacitance) depends on the frequency of the current—measurements of basic resistance between electrodes while using a number of electrodes, typically at three different preferred frequencies (16, 100 and 200 kHz), are examples of frequencies used in the preferred embodiment—and allows the calculation, by three mathematical equations, of the values of:

Brain Tissue Impedance:
R1 (extracellular resistance),
R2 (intracellar resistance)
C (brain tissue capacitance)

and also the full brain tissue resistance (the complex impedance ReZ) and the reactance (ImZ). In addition, the software can also preferably calculate the ratio of reactance and resistance $tg\varphi = ImZ/ReZ$—the phase angle of brain bio-impedance.

The software of the preferred embodiment preferably calculates and delivers these mathematically calculated values automatically from the basic resistance. This approach allows the separation of extracranial components from the intracranial components as they are represented in the values of the basic resistance between electrodes. Failure to separate these components had previously been the main deterrent and limitation to widespread use of the rheoencephalograph method as a "stand alone" method for cerebral investigations.

Underpinning the present analysis is the concept that the amount of "water" that a cell takes on in the brain is of critical importance in brain injury management. This is as important to the brain as is the cardiovascular competence level of the heart/lung/body to the human body maintaining homeostasis.

The individual should be able to maintain body "homeostasis"—when the person cannot "auto-regulate" then he/she has exceeded reasonable physiologic capacity. This invention provides a means whereby the physiological aspects of the head and/or body related to the distribution of fluids can be monitored and displayed in near real time.

More particularly, the present invention relates to monitoring head and/or body segment impedances for determining fluid volumes and fluid flows in a head and body in near real time.

Blood pressure, temperature, ECG, chest respiratory movements and the oxygen and carbon dioxide saturation levels of the blood and blood flow characteristics may be incorporated and combined for analysing trends of the auto-regulation phase particular to an individual.

This invention provides an improved method of analysing physiological data using a rheoencephalograph combined with dopplerography and the specialized software platform (IAS).

In one embodiment, the computational device or computer and software are configured for determining fluid volumes and fluid flows in a head and/or body segment in at least near real time which overcomes or ameliorates one or more of the disadvantages or problems described above, or which at least provides a useful alternative. One embodiment of the invention discloses a critical near real time analysis combining and displaying different types of data simultaneously. This results in more time efficiency and effective decision-making by the treating physician, and the best choice of the correct medical intervention to be applied to the patient.

For the sake of convenience, the term "monitor" should be understood to mean one or more monitors.

The non-invasive monitor is preferably a rheoencephalograph and preferably a multi-frequency, multi channel rheoencephalograph combined with a doppler or ultrasound device.

Specifically the rheoencephalograph developed may operate on multiple frequencies simultaneously; or be electronically switched automatically by pre-set command between frequencies (16, 100, 200 Kilohertz) at an adjustable rate to record and calculate simultaneously the desired physiological data including the capacitance and resistance for different tissue structures—connective tissue vs. blood (intracellular fluid volume of one or more cells vs. extracellular fluid), and may be configured to display for head and/or body segments. In one embodiment, the monitor may be a single instrument with all fluids monitored down to intracellular and extracellular fluid levels. The doppler is configured in a manner allowing constant signal monitoring and data storage and retrieval by the software in order to generate the combined waveform from the rheoencephalograph and doppler data inputs.

The system may include at least two excitation electrodes for providing an electrical stimulus across selected head and/or body regions. The system typically also includes at least one or more monitoring electrodes.

The monitor may have a number of electrodes that are configured for placement in a non-invasive manner for effective operative engagement with the head or body; such that at least one electrode engages each of a number of selected segments of the head and/or body.

The monitor may be configured to use any number of different frequencies but three frequencies have been found to provide the optimum number of frequencies. This spread of frequencies provides sufficient information to allow calculation of all desired characterizing parameters.

The software of the preferred embodiment may be configured to store the impedance parameters and doppler signals; extract data segments relating to test sequences, combine the waveforms and produce the desired calculated data graphs, spectral analysis graphs and resultant calculations for display or storage into a database for subsequent access and comparison of the subject's physiological conditions. Furthermore, the software preferably allows queries to be run on the database to provide comparative analysis based on a cumulative database structure enabling detection of anomalous subject conditions. An array of subject tests can be configured to allow different subject test results to be compared on a multiple display. Near real time monitoring of the subject's physiologic condition can be relayed to a larger screen via HDMI or VGA output.

The software of the preferred embodiment may be configured to output the characterizing data in any one or more of the following forms:

a) near real-time;
b) replay of previously recorded characterizing data; and/or
c) together with mathematically reconstructed waveforms or graphs.

According to a second aspect of the invention, there is provided a method for measuring physiological characteristics, the method comprising the steps of:

engaging a non-invasive monitor(s) with a body, the non-invasive monitor being configured to generate data and monitor signals relating to fluid characteristics in the body;

processing the data to generate characterising analyses relating to at least one of regional fluid volumes, intra/extracellular fluid volume ratios and blood flow; and outputting the characterizing data.

The step of engaging a non-invasive monitor(s) with the body may include the step of engaging an electrode montage with the body such that any one or more segments of the body are monitored, combining for example a head segment, a chest segment, a splanchnic segment, a pelvic segment and a leg segment.

The chest segment, the splanchnic segment, the pelvic segment and the leg/arm segments may be monitored using an initial instance of the rheoencephalograph, while the head segment may be monitored using a second instance of the rheoencephalograph and doppler.

The step of processing the monitor signals may include the step of processing the monitor(s) signals to generate resistance and reactive capacitance data and to process the combined waveform data from the rheoencephalograph and doppler and to input that data to generate the characterizing data.

The step of outputting the characterizing data may include the step of normalizing the data and displaying the data visually and/or outputting in a computer readable form.

The characterizing data may be outputted in any one or more of the following forms:
a) near real-time;
b) replay of previously recorded characterizing data; and/or
c) together with mathematically reconstructed waveforms.

It follows that the system and method of the invention output and monitor fluid data, including fluid movement data, between the brain/head, chest, abdomen, pelvis, thigh, lower legs, and arms regions of a body. The output fluid information of these body regions may provide descriptions of the hemodynamic and volume responses in a human body in conjunction with other physiological data.

The output may be used to characterize regional fluid volumes, intra/extracellular fluid volume ratios, hemodynamic status and blood flow in near real time during clinical and research protocols that allow the quantification of segmental blood flows, total segmental volumes, and segmental compartment volumes in near real time. In the event of trauma and in the absence of outward signs of injury, the detection of abnormal blood pooling or flow is critical in the diagnosis and application of specific treatment.

The computer may be programmed with a software product, in accordance with the invention, such that the computer uses a de-convolution algorithm on data obtained from the microprocessor system to obtain parameters for an R-C equivalent circuit used to model the intravascular, interstitial and intracellular fluid spaces.

In one embodiment, the rheoencephalograph will be portable. Furthermore, the rheoencephalograph may be configured to independently monitor the fluid data itself.

The electrode leads may require shielding to prevent interference such as from environmental interference. The electrodes may be disposable EKG electrodes.

The instruments of the system and method may be battery powered, power supply powered, USB powered or a combination. A voltage level indicator may be provided on all battery powered devices (if any) and the voltage level is read prior to conducting tests to ensure adequate battery power is available for the tests.

According to a third aspect of the invention, there is provided a computer program product comprising a computer usable medium including a computer readable program for measuring physiological aspects, wherein the computer readable program, when executed on a computer, causes the computer to:
process data received from a non-invasive monitor(s) engaged with the body to generate characterizing data relating to at least one of regional fluid volumes, intra/extracellular fluid volume ratios and blood flow; and
output the characterizing data.

The computer readable program, when executed on a computer, may cause the computer to output the characterizing data in one of the following forms:
a) near real-time
b) a replay of previously recorded characterizing data
c) together with mathematically reconstructed waveforms.

The following description is not intended to limit the scope of the above paragraphs or the scope of the claims. As such, the purpose of the following description is to describe to a person of ordinary skill in the art how to put an embodiment of the invention into practice.

BRIEF DESCRIPTION OF THE DRAWINGS

In order that the invention may be more readily understood and put into practice, one or more preferred embodiments thereof will now be described, by way of example only, with reference to the accompanying drawings, in which:

FIG. 20 shows the extracted data in a table for the R1, R2, and C based on a test performed using the system illustrated in FIG. 13.

DESCRIPTION OF PREFERRED EMBODIMENT

Figure 1:
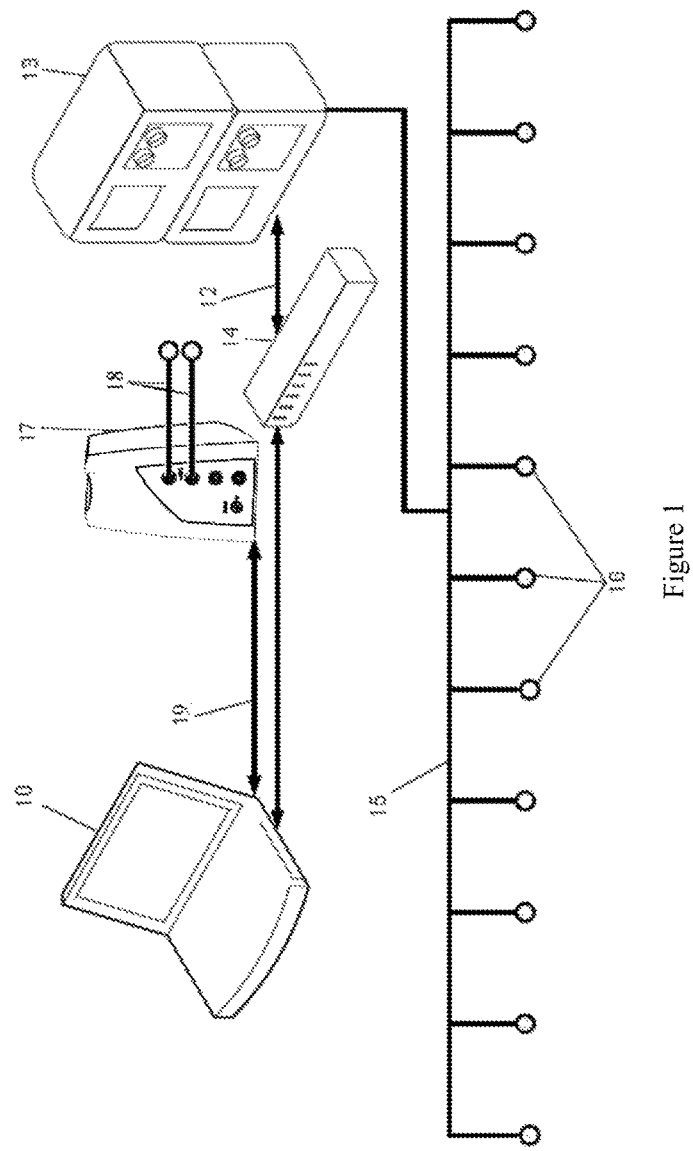
FIG. 1 shows a system, in accordance with the invention, for measuring physiological characteristics.

FIG. 1 shows broadly, a system, in accordance with the invention, for measuring physiological aspects of a body. The system includes a computer 10 that defines a computational device and a data output device of the invention. Output data 11 generated by the computer 10 can be graphs displayed on a screen of the computer 10, but may take any suitable form, such as tables or metrics. The computer 10 is connected to Multi Frequency REG rheoencephalograph monitors represented with reference 13 in FIG. 1, via a microprocessor system 14. A doppler system 17 with its own ultrasound sensors 18 is connected via cable 19. The computer 10 can be a stationary desktop model or preferably a laptop computer for portability. For the sake of convenience, the monitors will be referred to as the rheoencephalograph monitor 13 and doppler monitor 17.

In the embodiment shown in FIG. 1, the cable 12 is connected to the computer 10 using a universal serial bus (USB) interface, but it is envisaged that other interfaces could be used, such as wireless or Bluetooth.

Different frequencies can be selected for use by the Multi Frequency Multi Channel REG monitors 13; however 16 Khz, 100 Khz, and 200 Khz have been found to be the most suitable for the R1, R2 and C calculations. Where the monitor is a multi-frequency bio-impedance monitor, it uses a constant current transformer coupled excitation stage in conjunction with a digital demodulation stage to supply both resistive and reactive impedance components. Thus, the monitor 13 can be configured to generate monitor signals relating to fluid characteristics in the body; in this example, said fluid characteristics being resistive and reactive impedance components. The doppler system 17 stores blood flow data in the form of ultrasound waveform parameters and waveform segments prior to communicating the data to the computer 10 for processing to generate a combined doppler and rheoencephalograph waveform used to then generate characterizing data for on-line near real time analysis and display.

A software product, in accordance with the invention, when executed by the computer 10, uses a de-convolution algorithm applied to the impedance parameters and signal waveform segments to obtain parameters for an R-C equivalent circuit used to model the intravascular, interstitial, and intracellular fluid spaces as well as other required data.

Figure 2:
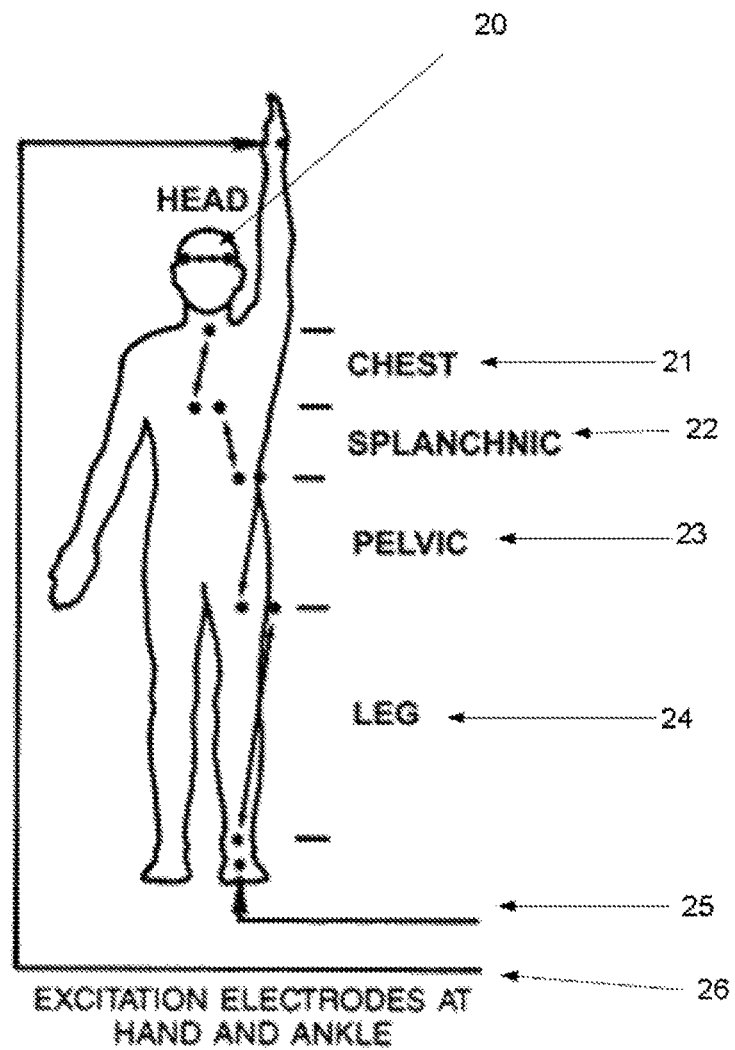
FIG. 2 shows one possible example of an electrode montage of the system, in use.

The monitor 13 is connected to a montage 15 having ten electrodes 16. As depicted in FIG. 2, a suitable electrode montage is provided which divides the body into five segments for segmental blood flows and volume change analysis. These is a head segment 20, a chest segment 21, a splanchnic segment 22, a pelvic segment 23, and a leg segment 24. The chest segment 21, splanchnic segment 22, pelvic segment 23, and leg segment 24 of the body are monitored by the monitor 13 using a rheoencephalograph impedance system. The head segment 20 is monitored by the rheoencephalograph monitor 13 and doppler monitor 17 configuration for monitoring cerebral (head) blood flow responses.

Figure 14:
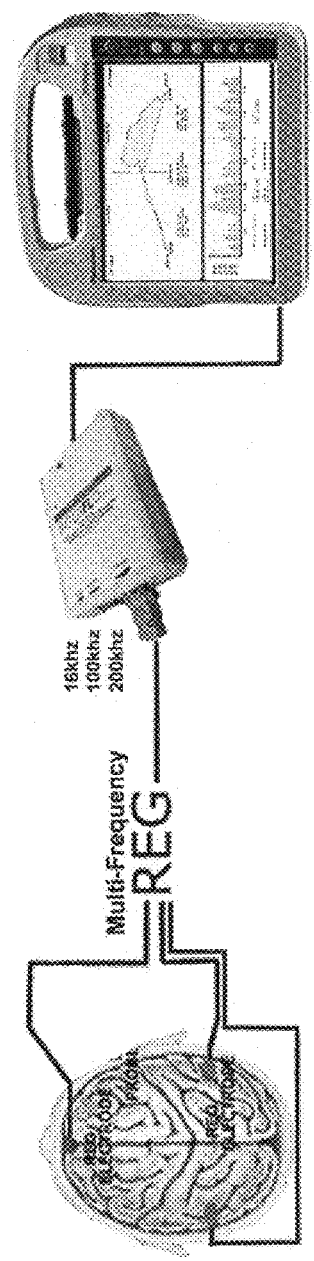
FIG. 14 shows one possible example of a portable system for field/emergency examination according to a preferred embodiment.
Figure 15:
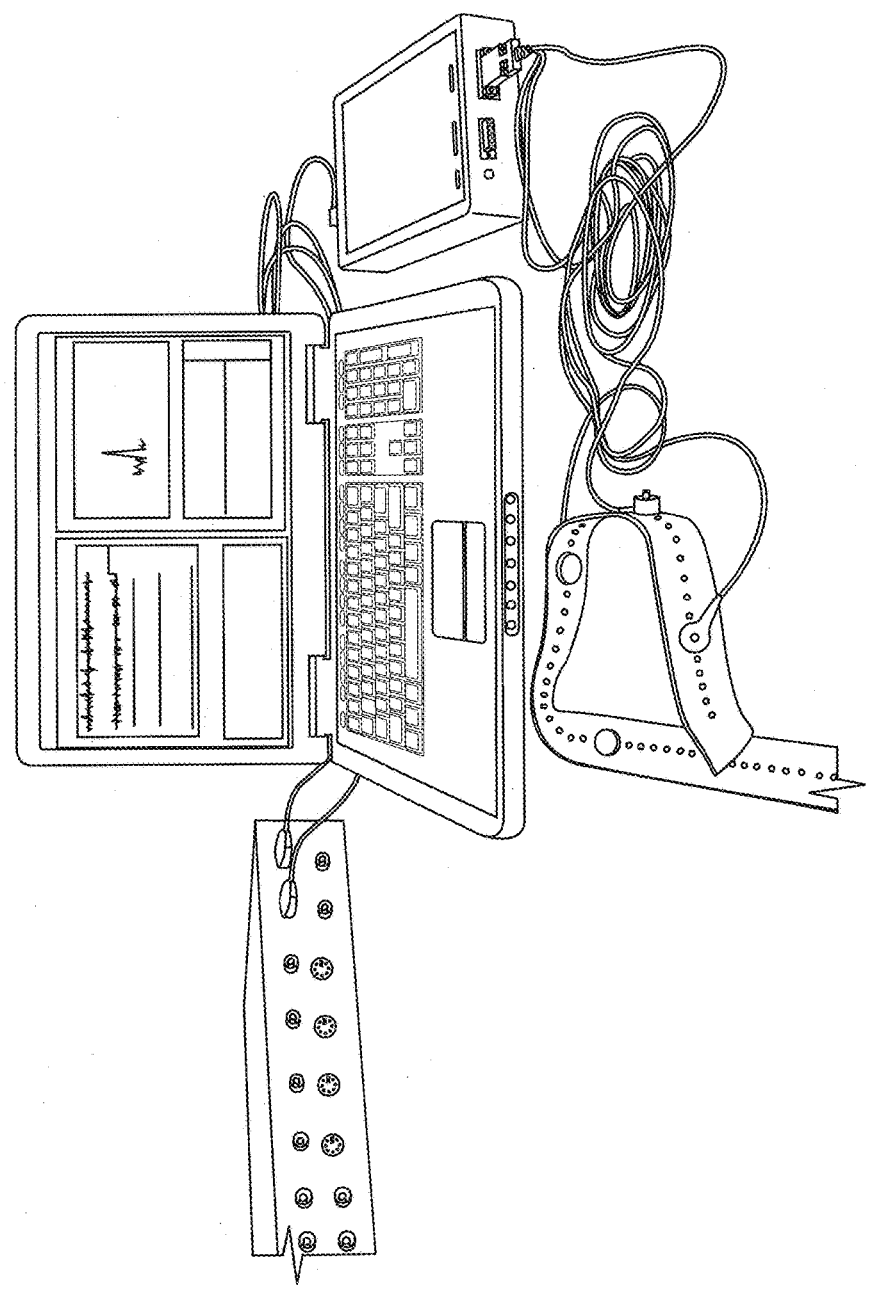
FIG. 15 shows the rheoencephalograph of a preferred embodiment connected to a laptop.
Figure 15:
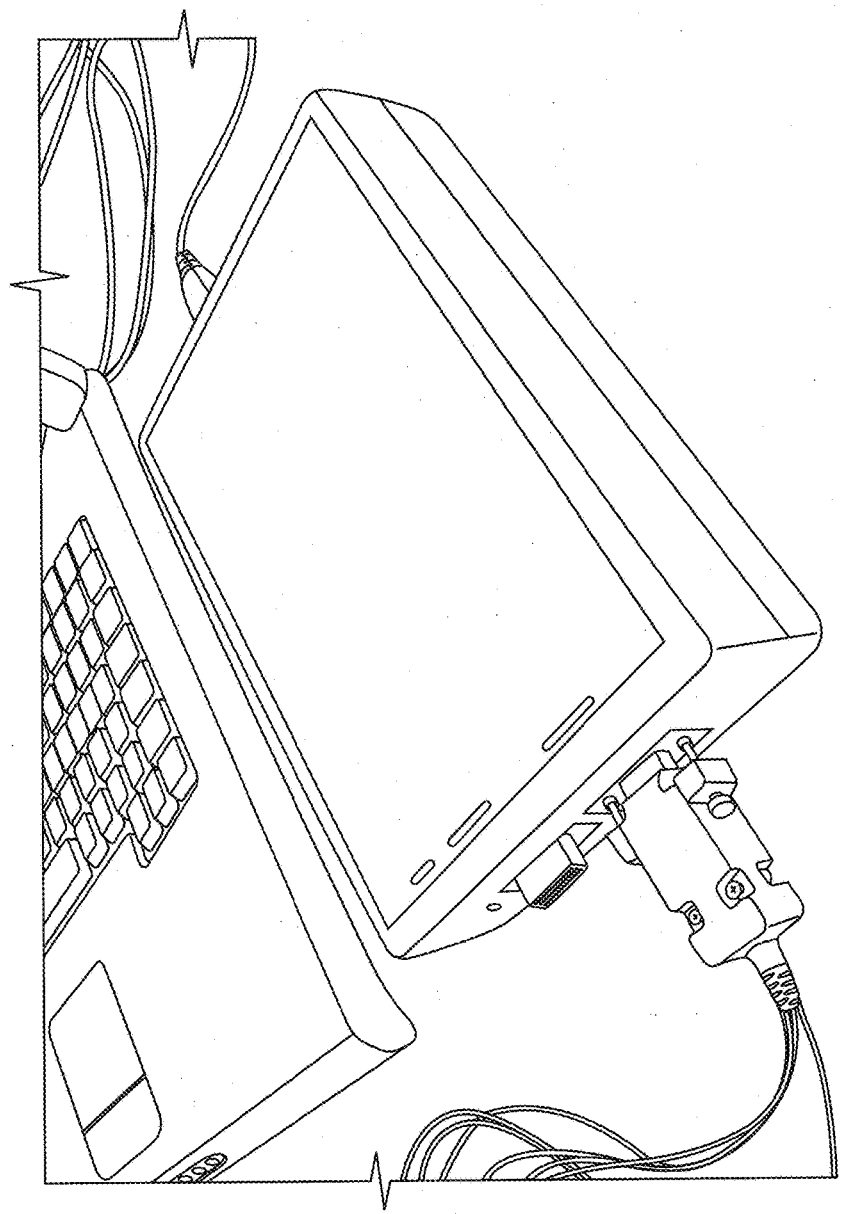

As depicted in FIG. 14, a suitable electrode montage is provided which attaches to the head and can also be configured to attach to the body segments for segmental blood flows and volume change analysis. Possible configurations are a head segment 20, a chest segment 21, a splanchnic segment 22, a pelvic segment 23, and a leg segment 24. The chest segment 21, splanchnic segment 22, pelvic segment 23, and leg segment 24 of the body are monitored by the monitor 8. Multiple monitors 8 can be used if more channels are required.

Electrodes 25 and 26 are excitation electrodes for supplying a minute electrical charge at different frequencies to the body to be read by the other electrodes.

The electrodes need shielding along the length of the electrode leads to prevent interference and artefacts such as from environmental interference. A suitable electrode is a general purpose disposable EKG electrode.

Figure 3:
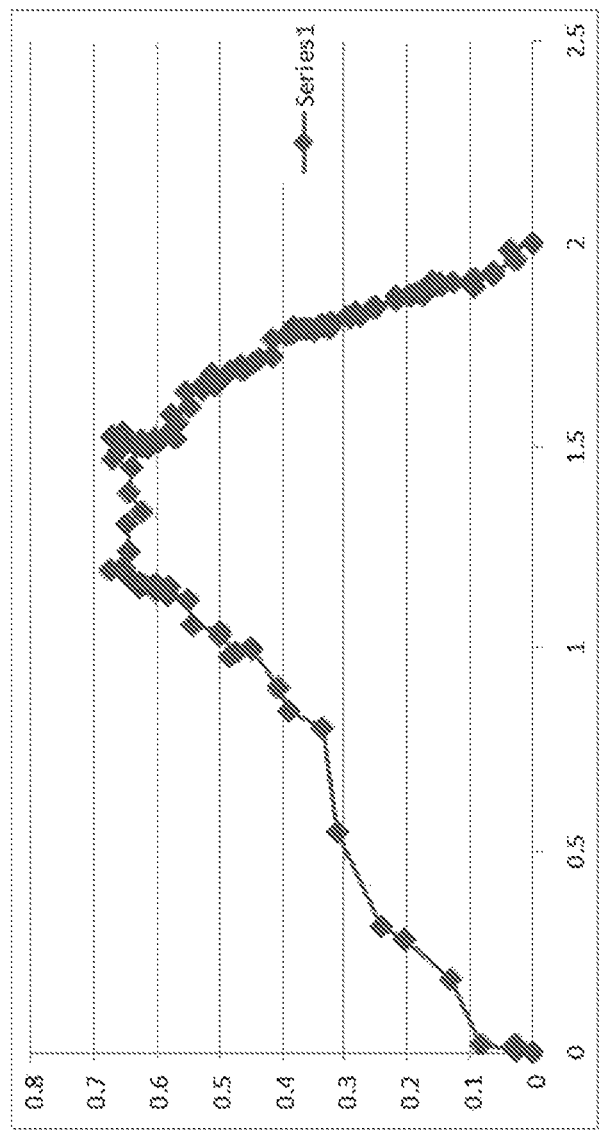
FIG. 3 shows an output of a unique new waveform generated by the coupling of the rheoencephalogaph and doppler waveform segments.

The unique waveform generated by the combination of the rheoencephalograph monitor 13 and the doppler monitor 17 are represented in FIG. 3.

A process of Transforming the Wave and a brief Summary thereof is set forth below:

1. Import text data from file or clipboard into IAS—the data is in the form of data points. This includes the Lab Chart header which details channel names and dates.

2. Synchronize the TCD doppler and REG impedance channels by matching the minimum points at the commencement of recorded segment.

3. The X or TCD doppler values are then scaled to cover the full width of the graphing area (preferably the arbitrary range 0 to 2 is used). The Y or REG impedance values are scaled proportionally to match these changes.

4. The Diastolic half of the wave has its REG (rheoencephalograph) values inverted to flip the axis as desired.

5. The Systolic is then plotted on the left side and should fit perfectly if scaled correctly in Step 3.

6. The Diastolic is then plotted on the right; however the ending point may be higher or lower than the baseline of the graph. The final point is extended to match the baseline.

7. The CSFm, angles, Delta V and Delta T are then calculated and displayed.

8. Data is saved into a database under the relevant de-identified and encrypted 'Subject' listing for retrieval using a filter query.

Impedance data can be recorded from the body segments in near real time and within a clinical environment. A vector board version can also be used to generate resistance or reactance recordings at various impedance sampling frequencies.

An aspect of the invention relates to the manner in which the data is collated and organised for analysis. Accordingly, the software product of the invention is configured to facilitate such collection and organization. FIGS. 4 to 12 are flowcharts that represent a method of collecting and processing data generated by the invention system. In particular, the software product of the invention is configured so that when executed by at least the computer 10, at least the computer 10 carries out the steps indicated in these flowcharts. For convenience, this example is described assuming that only the computer 10 carries out the steps of the method. Thus, in the following description, the phrase "the computer 10 carries out . . . " should be understood to mean that, when the software product of the invention is executed by at least the computer 10, at least the computer 10 carries out the relevant step. In light of that, it is to be appreciated that the steps as set out below can readily be carried out on one or more further dedicated computer components.

Figure 4:
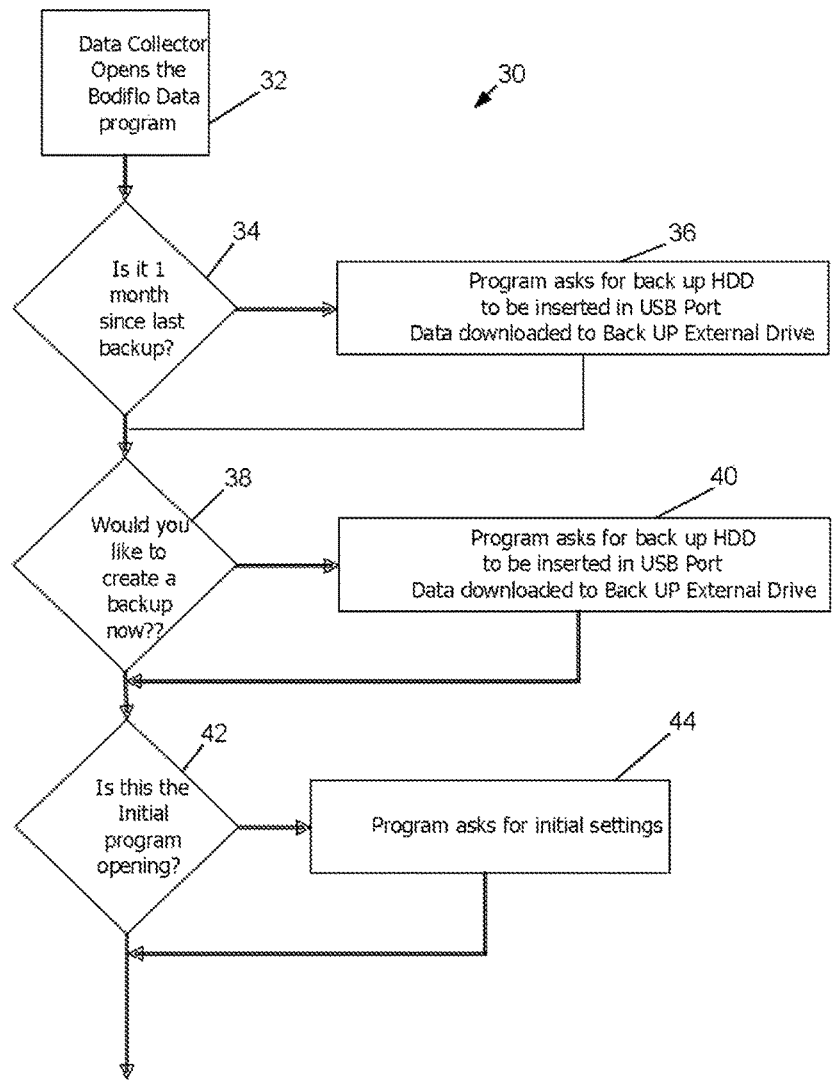
FIG. 4 shows a flow chart indicating an initial stage of a method, in accordance with the invention, carried out by a system, also in accordance with the invention, when a software product, also in accordance with the invention, is executed by components of the system.

In FIG. 4, reference 30 generally indicates a flow chart representing a data collection method carried out when the software product is executed. At 32, the software product initiates a method by opening the program of the software product. At 34, the computer 10 queries a user as to the time when the collected data was previously backed up. If the response is such that the data was backed up more than a predetermined period of time ago, the computer 10 requests that the user engage some form of removable storage device or media with the computer 10, at 36. If the response is such that the data was backed up less than said predetermined period of time ago, the computer queries as to whether or not the user would like to create a backup, at 38. If the response is positive, the computer requests that some form of removable storage device or media be engaged with the computer 10, at 40. Otherwise, the computer 10 queries as to whether this particular opening is an initial opening at 42.

Figure 5:
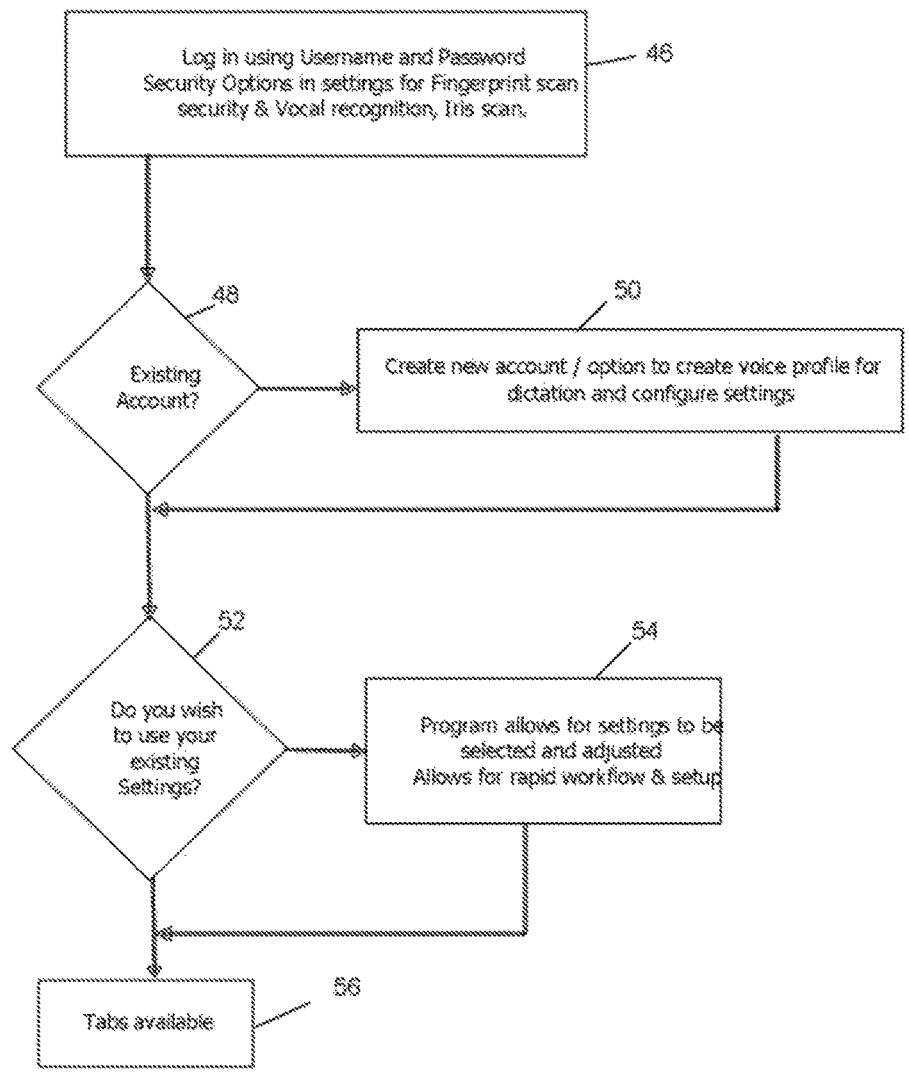
FIG. 5 shows a flow chart indicating a log in stage of the method of FIG. 4.

If the response is positive, the computer 10 requests the input of initial settings at 44. Otherwise, the computer 10 requests that the user log in using his or her log in details at 46 (FIG. 5). The log in details are preferably any one of fingerprints, iris scans or other biometric identifiers.

The computer 10 then queries whether or not the user is logged in to an existing account at 48. If the answer is negative, the computer 10 creates a new account and/or options to create a new voice profile for dictation and configures the settings at 50. Otherwise, the computer 10 queries whether or not the user wishes to use his or her existing settings, at 52. If the answer is positive, the computer 10 allows for settings to be selected and adjusted and also allows for workflow and set up to be carried out, at 54. Otherwise, the computer 10 makes a number of tabs available for the user at 56.

Figure 6:
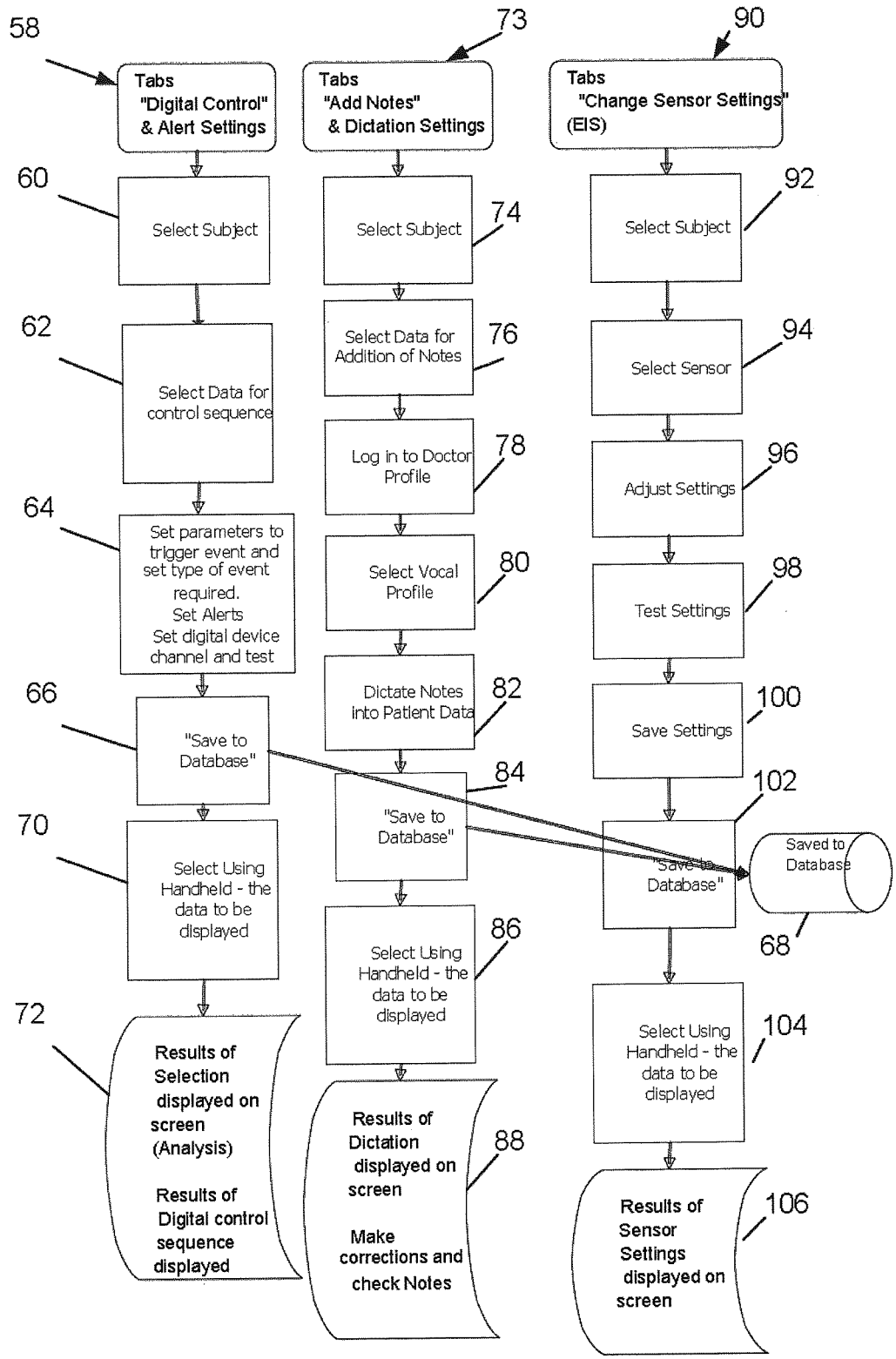
FIG. 6 shows a flow chart indicating a digital control and 'alert settings' stage, a stage for adding nodes and setting dictation characteristics, and a stage for changing sensor settings.

In FIG. 6, reference 58 generally indicates a flow chart for allowing a user to select digital control and alert settings. At 60, the computer 10 allows the user to select a particular subject who is being tested. At 62, the computer 10 allows the user to select data for controlling a sequence of steps. At 64, the computer 10 allows the user to set the necessary parameters to trigger events and to set the type of events required. Alerts and a digital device channel are also set and tested. At 66, the computer 10 saves data input at 60, 62, 64 to a database 68. At 70, the computer 10 allows the user to display the data selected with a handheld device. At 72, the results of the selection are displayed on a screen for analysis and results of a digital control sequence are also displayed.

Reference 73 generally indicates a flow chart for allowing a user to add notes and to select dictation settings. At 74, the computer 10 allows the user to select a particular subject being tested. At 76, the computer 10 allows the user to select data for the addition of notes. At 78, the computer 10 allows the user to log into a particular profile of a doctor. At 80, the computer 10 allows the user to select a particular vocal profile. At 82, a computer 10 allows noted to be dictated into patient data. At 84, the computer 10 allows the user to save dictated data to the database 68. At 86, the computer 10 allows the user to display the data selected with a handheld device. At 88, the computer displays the results of the dictation on the screen and the user is permitted to make corrections and to check notes.

Reference 90 generally indicates a flow chart for allowing a user to add notes and to change sensor settings. At 92, the computer 10 allows the user to select a particular subject being tested. At 94, the computer 10 allows the user to select a particular sensor having settings to be changed. At 96, the computer 10 allows the user to adjust those settings. At 98, the computer 10 tests the settings. At 100, the computer 10 saves the settings. The settings are saved to the database 68 at 102. At 104, the computer 10 allows the user to display the data selected with a handheld device. At 106, the computer 10 displays the results of the sensor settings.

Figure 7:
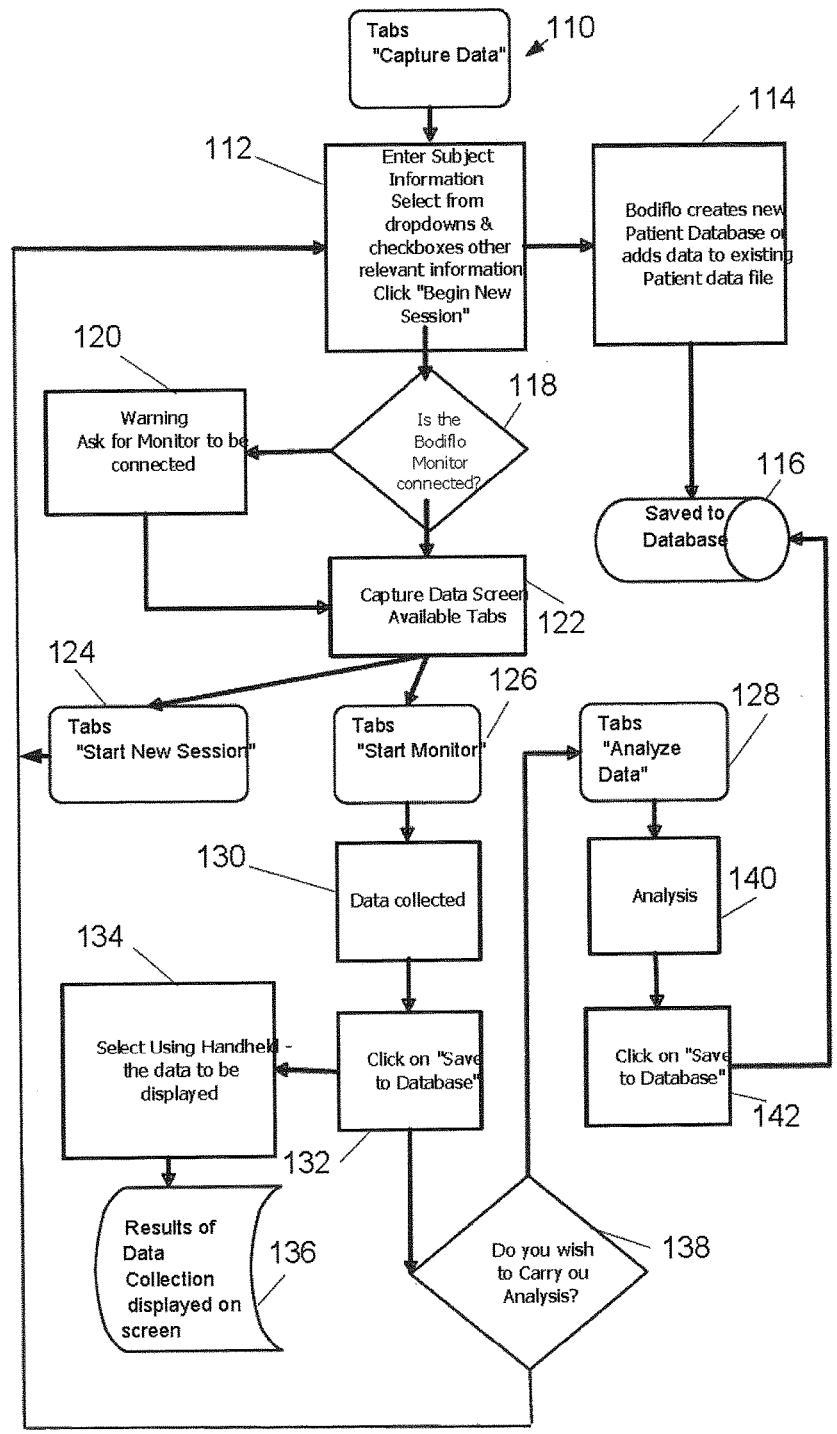
FIG. 7 shows a flow chart indicating a stage for capturing data.

In FIG. 7, reference 110 generally indicates a flow chart for allowing a user to capture data with the computer 10 executing a software product of the invention.

At 112, the user is prompted to enter information regarding the subject. This can be done by way of drop-downs and checkboxes. At 114, the computer 10 creates a new patient database or adds the patient data to a data base at 116. The computer 10 then queries as to whether the relevant monitor is connected at 118. If the response is negative, the computer 10 generates a warning, at 120, for connection of the monitor to the patient. If the response is positive, the computer 10 generates a number of tabs, at 122 for capturing data. More specifically, the computer 10 generates a "start new session" tab at 124, a "start monitor" tab at 126 and an "analyse data" tab at 128.

If the tab 126 is selected, the computer 10 collects the data at 130. At 132, the user is able to select a command for the computer 10 to allow the user to select data to be displayed using a handheld device at 134. At 136, the results of the data collection are displayed on a screen. If the user selects the command at 132, the computer 10 queries a user as to whether or not he or she wishes to carry out an analysis, at 138. If the response is positive, the computer 10 displays the tab 128. Then, the computer 10 performs the analysis at 140. The user is then prompted to save the results of the analysis, at 142, to the database at 116. Otherwise, the computer 10 returns to the step at 112.

Figure 8:
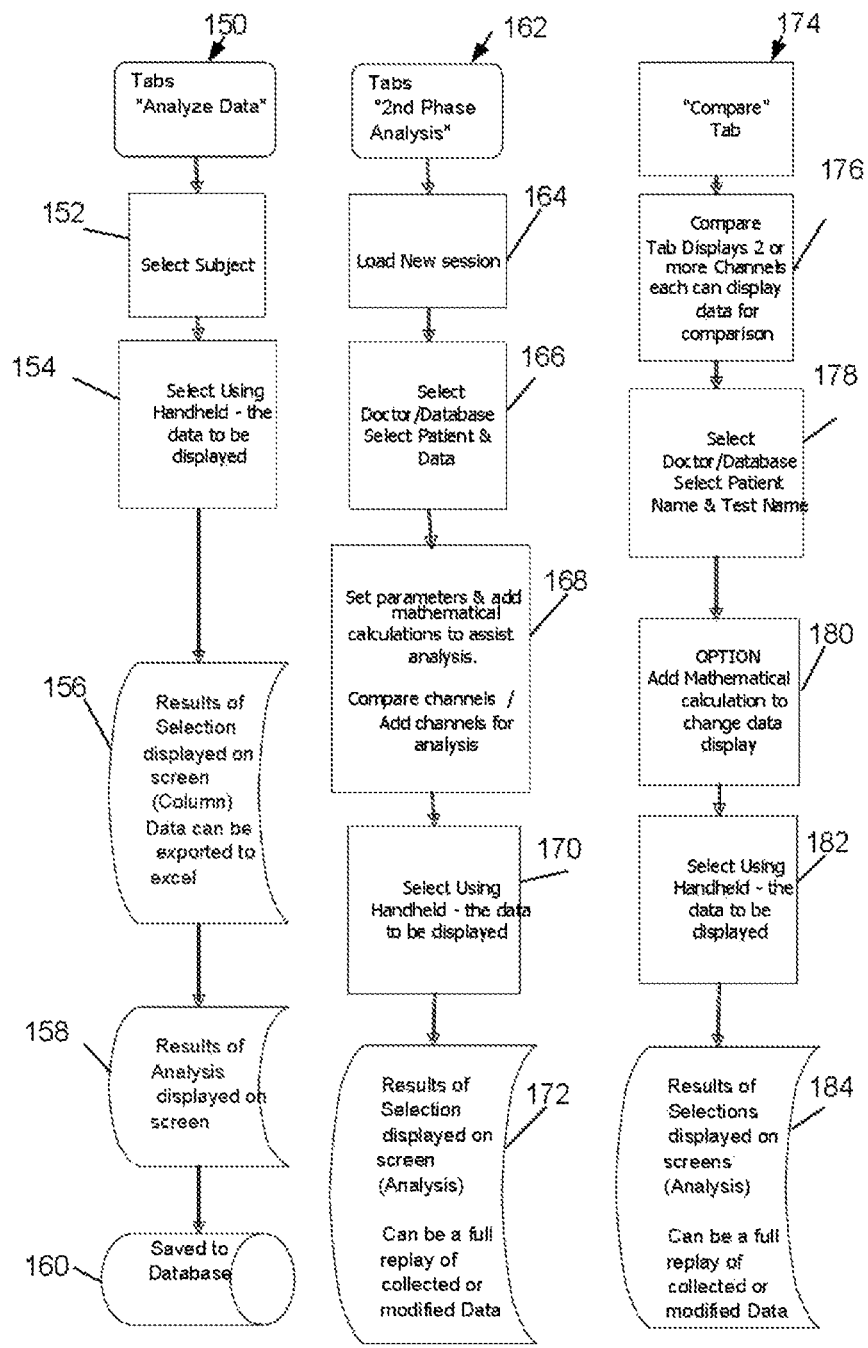
FIG. 8 shows a flow chart indicating a stage for analyzing data, a stage for carrying out a second phase analysis on the data, and a comparison phase.

In FIG. 8, reference 150 generally indicates a flow chart representing the possible steps subsequent to the "analyse data" tab being selected. At 152, the user is prompted to select a subject. At 154, the user is prompted to select, using a handheld device, data to be displayed. At 156, the results of the selection are displayed on a screen and the computer 10 is able to export the data to a spread sheet application. At 158, the computer 10 displays the results of the analysis on a screen. At 160, the results are saved to a database.

Reference 162 generally indicates a flow chart representing the possible steps subsequent to a "second phase analysis" tab being selected. At 164, the computer 10 loads a new session. At 166, the computer 10 allows the user to select a doctor or a database and also to select a patient and data relating to the patient. At 168, the computer 10 sets parameters and adds relevant mathematical calculations to assist the analysis. Also at 168, channels representing data from different regions sensed by the monitor 13 can be compared. Also, at 168, the computer 10 can add further channels for analysis. At 170, the computer 10 allows the user to select the data to be displayed with a handheld device. At 172, the computer 10 displays the results of the selection on a screen. This can be a full replay of the collected data or modified data.

Reference 174 generally indicates a flow chart representing the possible steps subsequent to a "compare" tab being selected. At 176, the computer 10 displays two or more of the channels such that the data represented by the channels can be compared. At 178, the computer 10 allows the user to select a doctor or a database and also to select a patient and data relating to the patient. At 180, the computer 10 allows an option to add a mathematical calculation or algorithm to change the data displayed. At 182, the computer 10 allows the user to select data to be displayed with a handheld device. At 184, the computer 10 displays the results of the selection on screens. As before, this can be a full replay of the collected data or it can be modified data.

Figure 9:
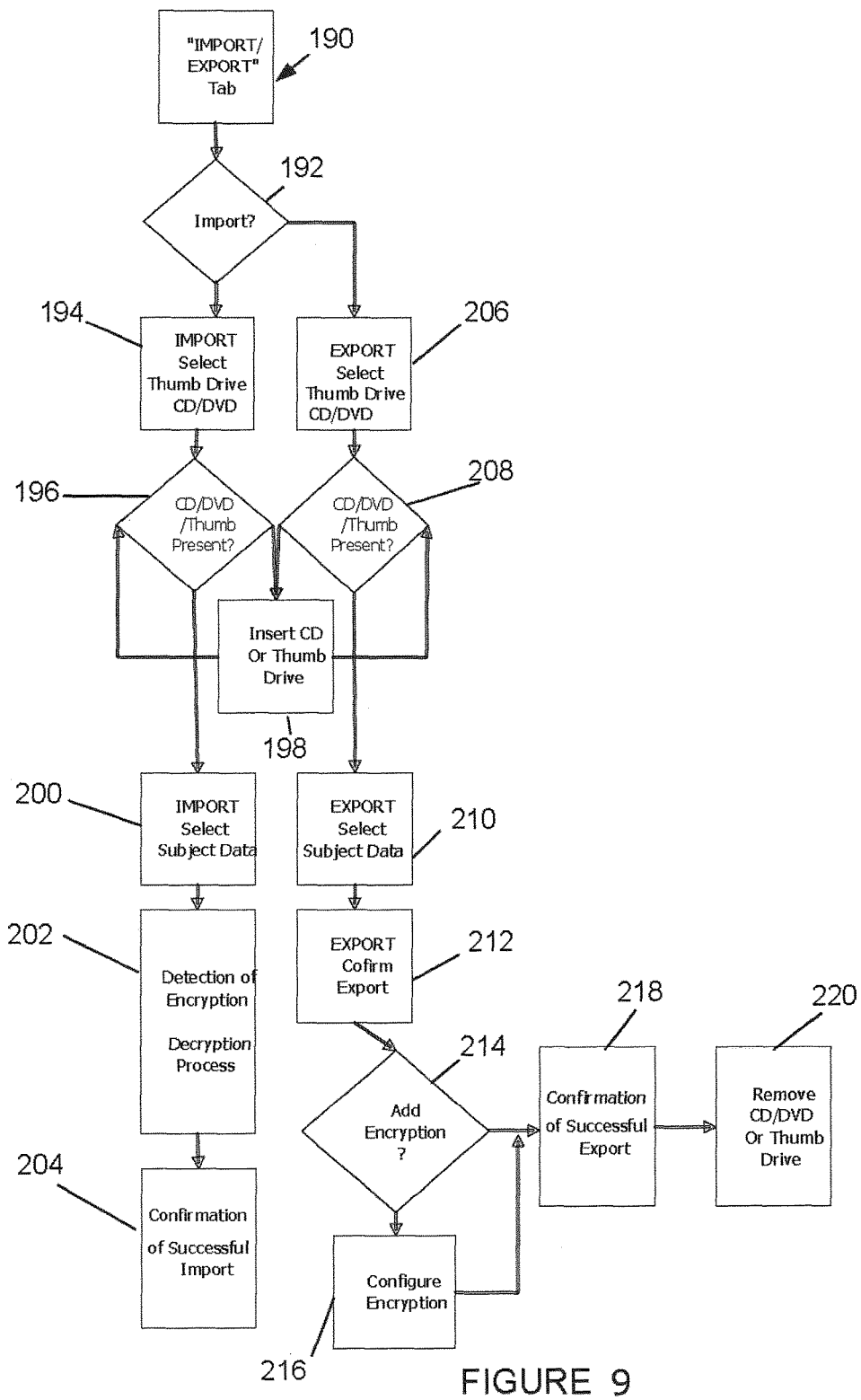
FIG. 9 shows a flow chart indicating a stage for either importing or exporting data.

In FIG. 9, reference 190 generally indicates a flow chart representing the possible steps subsequent to an "import/export" tab being selected At 192, the computer 10 queries whether or not data should be imported. If the response is positive, the computer 10 requests the user to select a source, such as a thumb drive, CD or DVD, at 194. At 196, the computer 10 queries as to whether or not the relevant source is present. If the answer is negative, the user is prompted to engage the relevant source with the computer 10, at 198. If the answer is positive, the computer 10 imports the relevant data, in this case data relating to the subject, at 200. At 202, the computer 10 detects whether or not encryption is present in the source and carries out a decryption process. At 204, the computer 10 confirms successful importation.

If the response to the query at 192 is negative, the computer 10 prompts the user to select a source, such as a thumb drive, CD or DVD, at 206. At 208, the computer 10 queries as to whether or not the relevant source is present. If the answer is negative, the user is prompted to engage the relevant source with the computer 10, at 198. If the answer is positive, the computer 10 exports the relevant data, in this case data relating to the subject, at 210, to the relevant source. At 212, the computer 10 confirms that the data has been exported. At 214, the computer queries whether or not encryption of the data is required. If the answer is positive, the computer 10 carries out an encryption process at 216. At 218, the computer 10 confirms successful exportation. At 220, the user is prompted to remove the relevant source.

Figure 10:
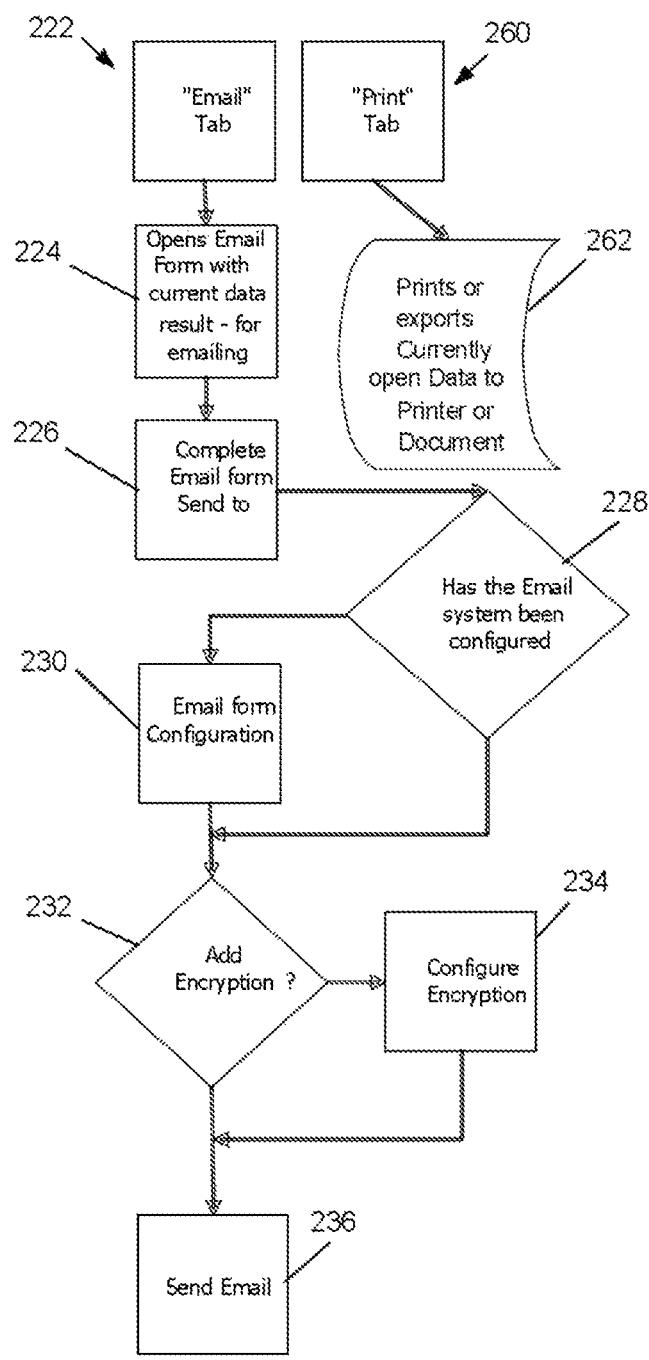
FIG. 10 shows a flow chart indicating a stage for either e-mailing or printing data.

In FIG. 10, reference 222 generally indicates a flow chart representing the possible steps taken by the computer 10 when an "e-mail" tab is selected. At 224, the computer 10 opens an e-mail form in which a current data result is represented. At 226, the computer 10 prepares the e-mail form for sending, once it has been completed. At 228, the computer 10 queries as to whether or not an e-mail system has been configured. If the response is negative, the computer 10 carries out an e-mail form configuration process at 230, and queries, at 232, as to whether or not the form should be encrypted. If the response is positive, the computer 10 moves directly to the query at 232. If the response to the query at 232 is positive, the computer 10 carries out an encryption process on the form at 234 and sends the e-mail form at 236. If the response to the query is negative, the computer 10 moves directly to the step of sending the e-mail form at 236.

Reference 260 generally indicates a step taken when a "print" tab is selected. At 262, the computer 10 prince or exports currently displayed data to a printer or to a further document.

Figure 11:
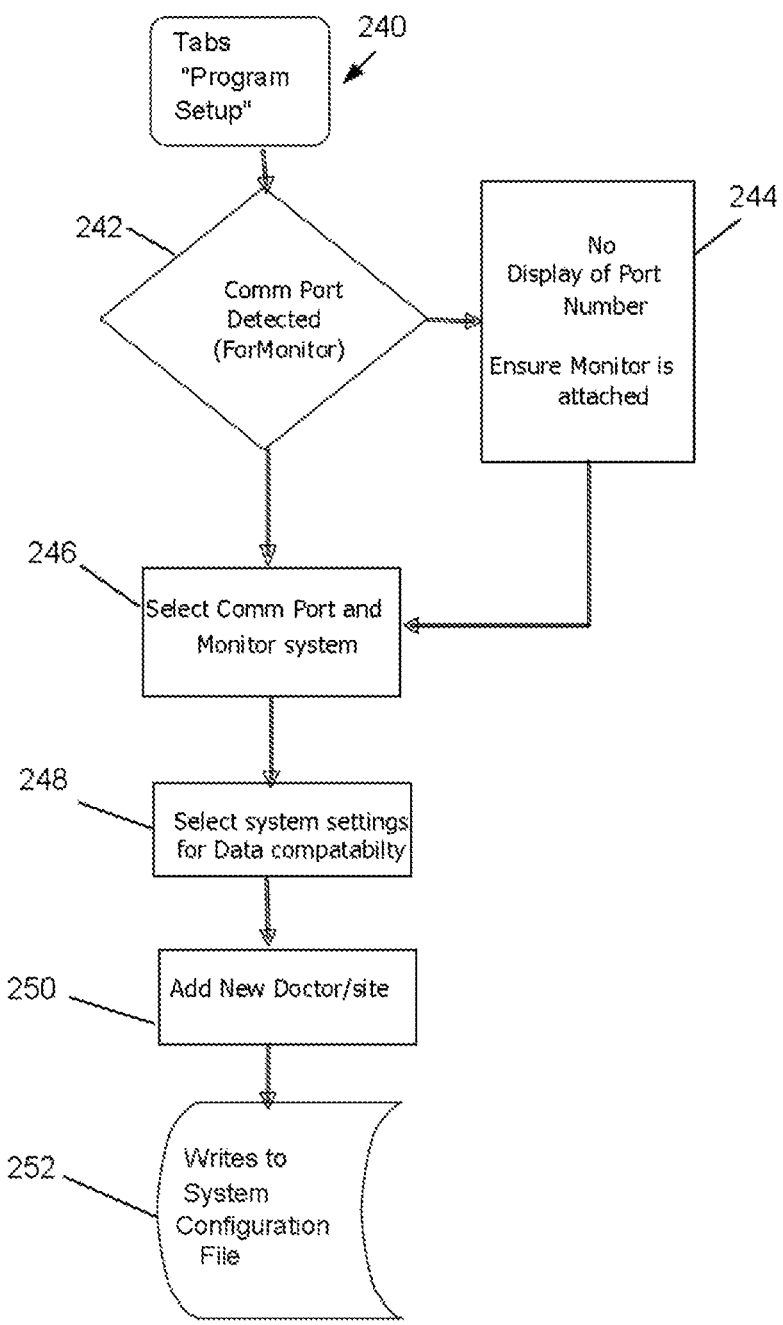
FIG. 11 shows a flow chart indicating a stage for setting up hardware that executes the software product.

In FIG. 11, reference 240 generally indicates a flow chart representing the possible steps taken by the computer 10 when a "program setup" tab is selected. At 242, the computer 10 queries whether or not a communications port has been detected. If the response is negative, the user is prompted to ensure that the monitor is properly attached at 244. If the response is positive, the user is prompted to select the communications port and the monitor system, at 246. At 248, the computer 10 selects relevant system settings for data compatibility. At 250, the computer 10 adds doctor or site data. At 252, the computer 10 writes the setup data to a system configuration file.

Figure 12:
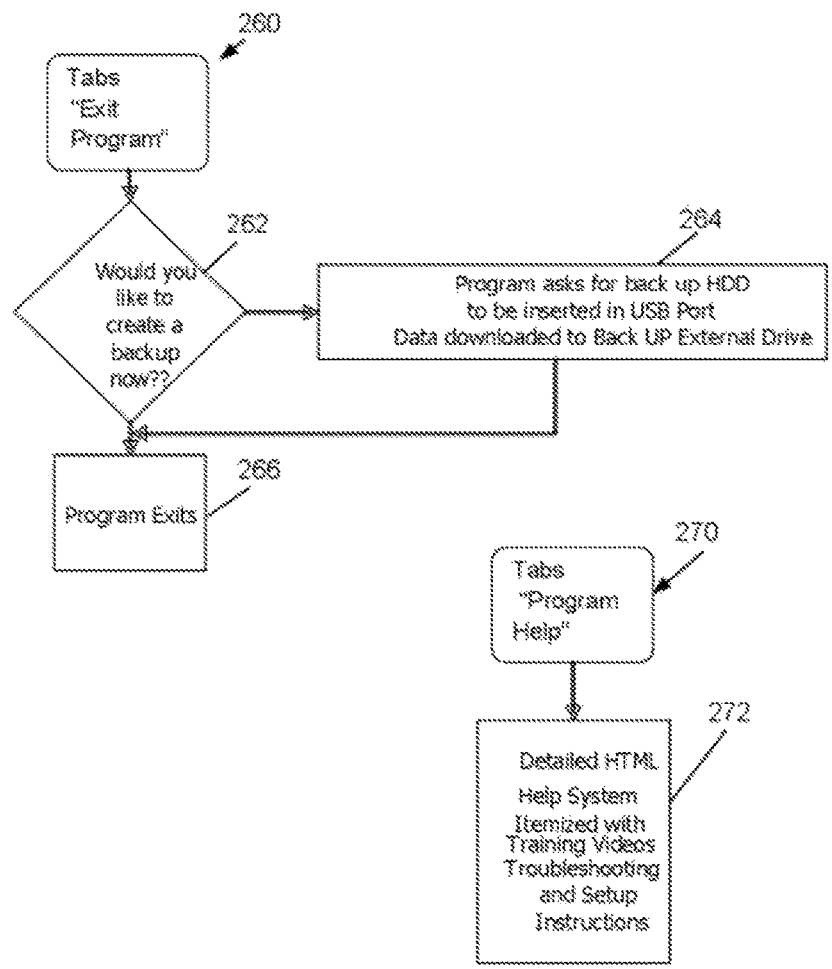
FIG. 12 shows a flow chart indicating a stage for exiting a software product and a stage for selecting help.

In FIG. 12, reference 260 generally indicates a flow chart representing the possible steps taken by the computer 10 when an "exit program" tab is selected. At 262, the computer 10 queries whether or not a backup of the data should be created. If the response is positive, the computer 10 prompts the user, at 264, to insert the relevant removable media to which the data to be backed up is to be written. Also at 264, the data to be backed up is written to the removable media. The computer 10 exits the program at 266. If the response is negative, the computer 10 moves directly to the step at 266.

Reference 270 shows the possible step taken when a "program help" tab is selected. The computer 10 generates a detailed HTML help system that is itemised with training videos, troubleshooting and setup instructions, at 272.

The invention may be useful in the treatment of diverse pathophysiologic fluid volume states including, for example, the management of increased intracranial pressure following trauma, the treatment of disequilibrium and hypotension during renal dialysis, the monitoring of the hydrational state of premature infants, and the investigation and diagnosis of orthostatic intolerance associated with dysautonomia.

The impedance/doppler system can be used to assess the possible compartment changes monitoring two body segments at the same time. In this way, it will provide information regarding the fluid volume redistribution between two body segments in addition to the extent of intra/extravascular fluid shifts within a single body segment. In order to achieve this, the software product of the invention can be configured to be executed by the monitor 13. Thus, the monitor 13 can be configured to cooperate with other equipment to administer treatment to the subject. An example of this would be a dosage meter. In one embodiment, all computer programming will be applied to a small, portable system that can be used to monitor the intra/extravascular compartment volumes.

By continuous measurements of segmental blood flow and fluid volume changes, it will be possible to assess all of the individual fluid compartments of the body in terms of intracellular volume, interstitial volume, and intravascular volume.

Other areas of potential application of the invention include the hydration state of premature infants and burn patients, quantification of segmental and cerebral fluid shifts that take place during orthostatic tests and exposure to microgravity, and the assessment of various countermeasures designed to reduce the stress of re-entry.

The methodology explained above can be used with an alternative monitor in the form of a rheoencephalograph. Normally, at least a portion of the montage of electrodes are provide on a head band or similar attachment method adapted to be worn continuously by a test subject for the data collection period. The head hand may further include positioning portions to ensure as much as possible that the electrodes are positioned correctly on the subject's head for maximal data collection and accuracy.

Figure 13:
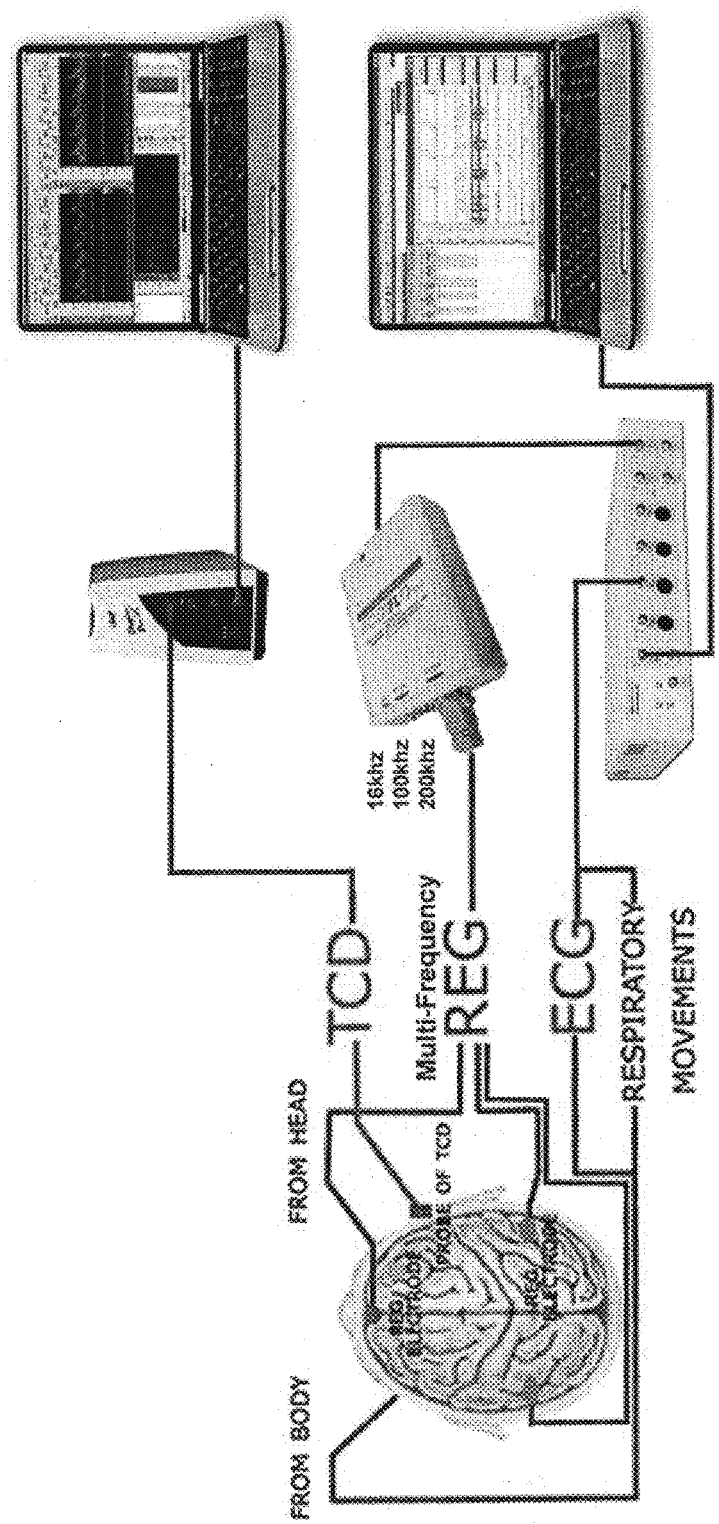
FIG. 13 shows a system, in accordance with the invention, for measuring physiological characteristics configured for laboratory examination and using the combined waveform from a rheoencephalograph and a transcranial doppler system.

FIG. 13 shows, broadly, a system, in accordance with the invention, for measuring physiological aspects of a body. The system includes a computer 10 that defines a computational device and a data output device of the invention. Output data 11 generated by the computer 10 can be graphs displayed on a screen of the computer 10, but may take any suitable form, such as graphs, tables or metrics. The computer 10 is connected to a rheoencephalograph 8. The computer 10 can be a stationary desktop model or preferably a laptop computer for portability. For the sake of convenience, the rheoencephalogaph will be referred to as the monitor 8.

In the embodiment shown in FIG. 13, the cable 12 is connected to the computer 10 using a universal serial bus (USB) interface, but it is envisaged that other interfaces could be used, such as wireless or Bluetooth.

Different frequencies can be selected for use by the monitor 8, however 16 Khz, 100 Khz, and 200 Khz have been found to be the most suitable for the R1, R2 and C calculations. Where the monitor(s) is a bio-impedance monitor, it uses a constant current transformer coupled excitation stage in conjunction with a digital demodulation stage to supply both resistive and reactive impedance components. Thus, the monitor 8 can be configured to generate monitor signals relating to fluid characteristics in the head or body; in this example, said fluid characteristics being resistive and reactive impedance components. The microprocessor system 14 stores data in the form of impedance parameters and signal waveform segments carried by the monitor signals prior to communicating the data to the computer 10 for processing to generate characterizing data for on-line near real time analysis and display.

The software in accordance with the invention, when executed by the computer 10, uses a de-convolution algorithm applied to the impedance parameters and signal waveform segments to obtain parameters for an R-C equivalent circuit used to model the intravascular, interstitial, and intracellular fluid spaces.

The rheoencephalograph 8 is connected to a montage 15 having multiple electrodes 16. As depicted in FIG. 13, a suitable electrode montage is provided which attaches to the head and can also be configured to attach to the body segments for segmental blood flows and volume change analysis.

The system illustrated in FIG. 13 shows a system, in accordance with the invention, for measuring physiological characteristics configured for laboratory examination and proof of concept. Specifically, the montage 15 is connected to a rheoencephalograph system 1801 but also to a TCD 1800 (transcranial doppler) system with a dedicated laptop for the TCD. The waveform segment from the rheoencephalograph and the doppler are combined in a transforming process to create a new unique wave which is then used to generate additional data and display and save this data for comparative analysis.

The rheoencephalograph laptop with the software for collating, calculating and displaying the physiological data is provided in association with the rheoencephalograph system but separately from the TCD in order to provide separate waveform captures for combination and further calculation of desired physiological characteristics. Other measurements can be taken such as through use of an electroencephalogram or EEG as illustrated.

FIG. 14 shows a portable configuration wherein the rheoencephalograph is battery powered, as is the portable computer, touchpad or smartphone.

Both devices in this example are battery powered. The rheoencephalograph in this example is using the automated calculation function in the software to perform the necessary calculations on this data and compute values for R1, R2 and C from this data and plot the changes during any single selected cardiac cycle.

The software is capable of being deployed on multiple platforms and can convey data feeds to a network for further analysis by a laboratory or display the subject's physiological data on its own screen.

Impedance data can be recorded from the head and body segments in near real time and within a clinical environment or in a field location. The data once saved to the database can be used to produce a calculation on selected parameters, produce spectrum and CVR graphs, and provide an interface whereby the user can view comparative tests or weigh the subject's results against a cumulative database to detect anomalous results.

The rheoencephalograph has the capacity to record steady state resistance on each frequency as well as the pulsing wave on 3 frequencies. The steady state resistance values will be received at a frequency of 100 times per cardiac cycle. Software has been automated to perform the necessary calculations on this data and compute values for R1, R2 and C from this data and plot the changes during any single selected cardiac cycle. The software product of this invention allows for configuration of the rheoencephalograph, control of the frequency selection, and retrieval, display and storage of the impedance data in a configurable graphed or tabled format.

The software is capable of exporting and importing data from other systems, automating backup procedures, capturing additional data for subjects using forms, has provision for administrators to create new test protocols and can create a cumulative database.

Figure 16:
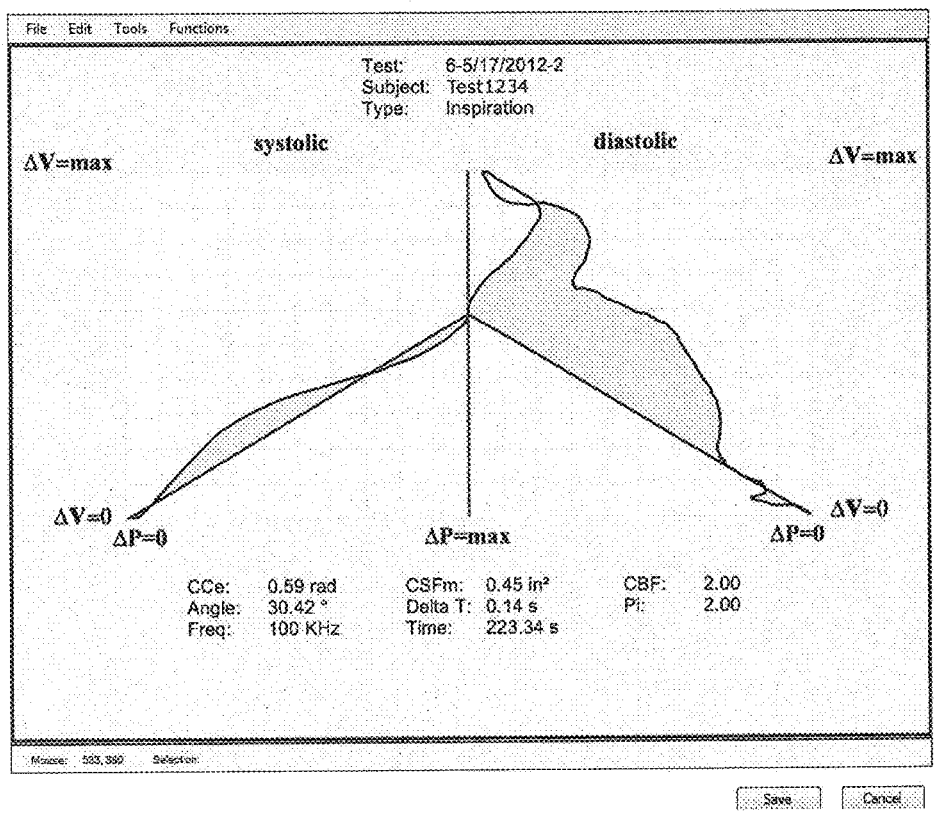
FIG. 16 shows an output of calculated data generated by the system of FIG. 13.
Figure 17:
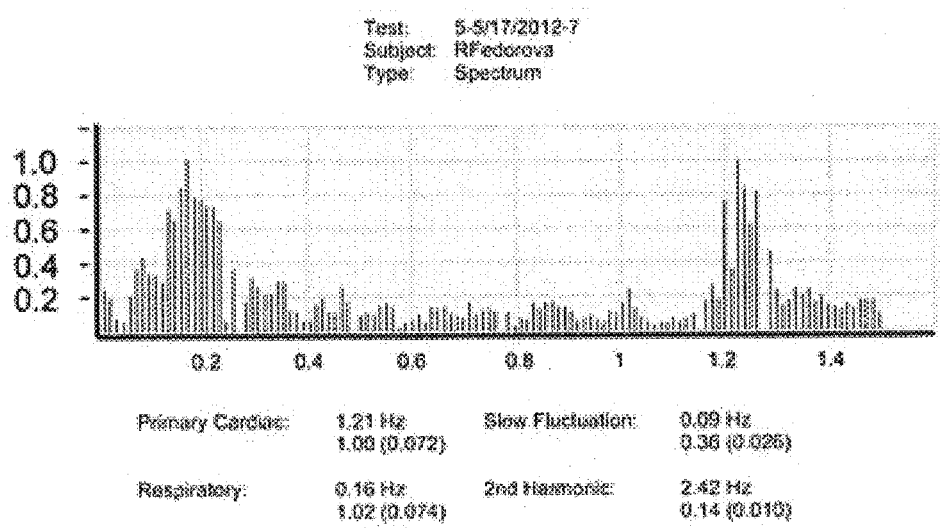
FIG. 17 shows an output of spectral data generated by the system of FIG. 13.
Figure 18:
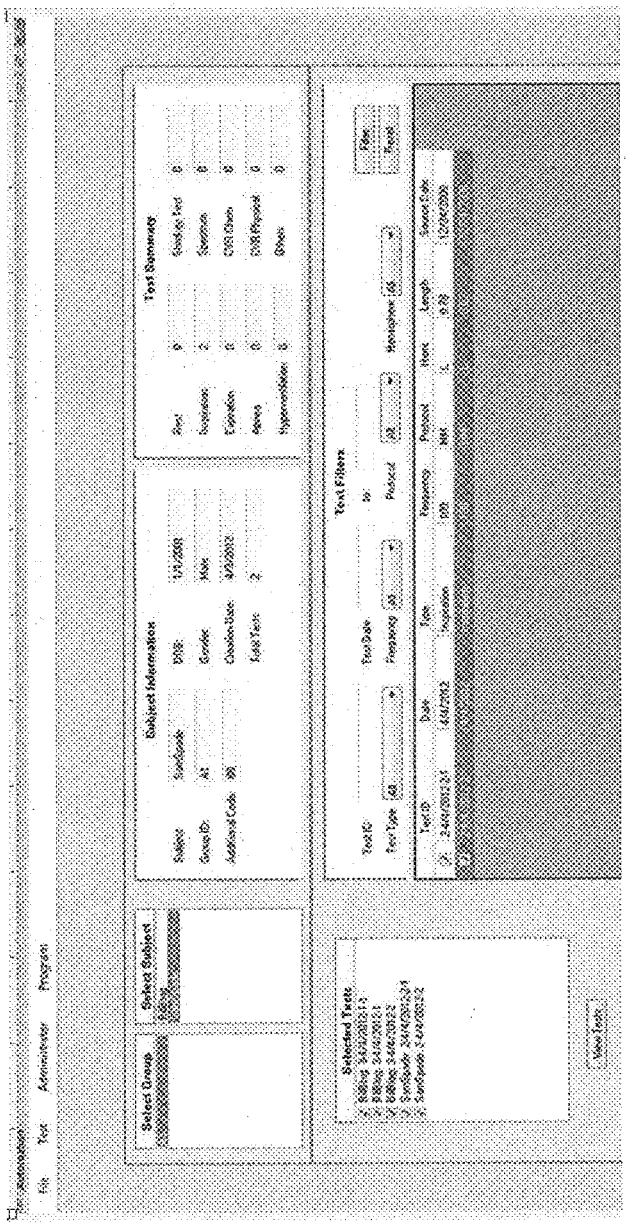
FIG. 18 shows the software test selection and test filter screen graphical user interface according to a preferred embodiment.

Example output results from the software are shown in FIG. 16 selected wave segment with calculated data displayed including these details:
Test Identifier
Subject Identifier
Test Type
Systolic Graph
Diastolic graph
CCe
Angle of systolic
Frequency of captured test
CSFm
Delta T
Time of the test (taken from recording track)
CBF
pi FIG. 17 shows a Spectral Analysis example including details:
Primary Cardiac
Respiratory
Slow fluctuation
$2^{nd}$ Harmonic FIG. 18 shows the software graphical user interface screen for test selection and allows for "Filtering" of subjects so that a comparative display of tests can be arranged. The "Test Summary" portion displays the tests that have been performed for this subject.

Figure 20:
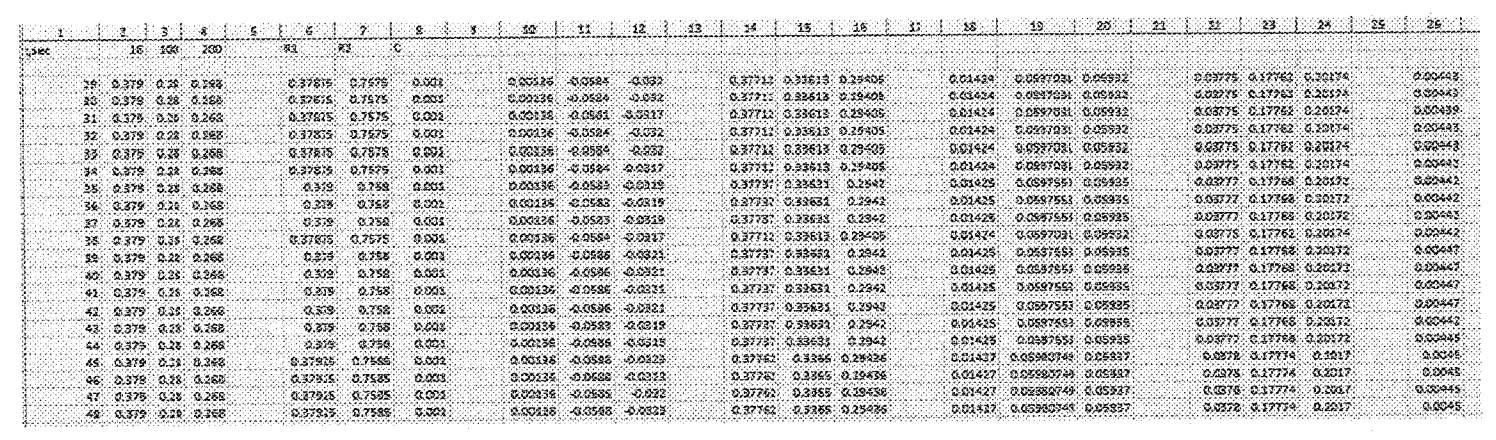

FIG. 20 displays an output table of CVR (physical) test results. CVR (Chemical) test results can be obtained also by selecting that function in the software.

Figure 19:
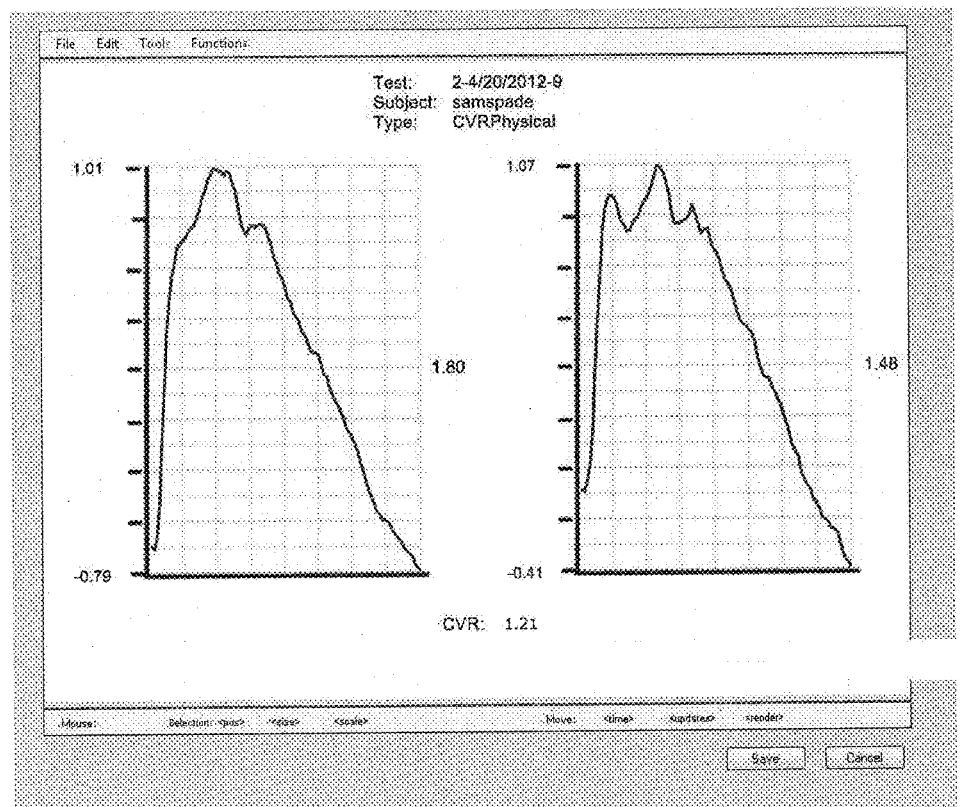
FIG. 19 shows the calculated CVR Physical (CVR Chemical is available also) in graphical form based on the information contained in the Table illustrated in FIG. 20.

FIG. 19, shows the resultant figures generated for R1, R2, and C (capacitance) from the information provided in the table in FIG. 20.

It is to be understood that the terminology employed above is for the purpose of description and should not be regarded as limiting. The foregoing embodiments are intended to be illustrative of the invention, without limiting the scope thereof. The invention is capable of being practised with various modifications and additions as will readily occur to those skilled in the art.

Accordingly, it is to be understood that the scope of the invention is not to be limited to the exact construction and operation described and illustrated, but only by the following claims which are intended, where the applicable law permits, to include all suitable modifications and equivalents within the spirit and concept of the invention.

It is envisaged that, although the invention has been described with particular reference to humans, it may also be applied to other bodies, such as animals.

Throughout this specification, including the claims, where the context permits, the term "comprise" and variants thereof such as "comprises" or "comprising" are to be interpreted as including the stated integer or integers without necessarily excluding any other integers.

The invention claimed is:

1. A system for measuring physiological aspects, the system comprising:
   a. a non-invasive monitor including a coupled transcranial Doppler and a multi-frequency rheoencephalograph, the monitor including at least one excitation electrode and at least one receiving electrode to be attached relative to a patient's head and configured to generate at least one excitation charge on at least one frequency and introduce said at least one excitation charge to the patient's head, and monitor at least one resistive impedance signal on the rheoencephalograph and at least one Doppler signal on the transcranial Doppler, the at least one resistive impedance signal and the at least one Doppler signal being recorded simultaneously over time in a number of cardiac cycles;
   b. a computational device operatively connected to the monitor and configured to process the at least one resistive impedance signal and the at least one Doppler signal in order to:
      i. synchronise the at least one resistive impedance signal and the at least one Doppler signal by matching a minimum point of the at least one resistive impedance signal at a beginning of a given cardiac cycle with a minimum point of the at least one Doppler signal at the beginning of the given cardiac cycle;
      ii. identify a systolic half and a diastolic half of the at least one resistive impedance signal and the at least one Doppler signal for the given cardiac cycle;
      iii plot the at least one Doppler signal on an X axis against the at least one resistive impedance signal on the Y axis for the given cardiac cycle, scaling the at least one Doppler signal, and scaling proportionally the at least one resistive impedance signal to match the sealing of the at least one Doppler signal to give a single waveform;
      iv. invert the diastolic half of the plot;
      v. align the systolic half of the plotted single waveform on a left side and the inverted diastolic half of the plotted single waveform on the right side to give a plot of a volume-pressure relation in the head for the given cardiac cycle; and
   c. a data output device connected to the computational device and configured to output the plot of the volume-pressure relation in the patient's head for the given cardiac cycle.

2. The system as claimed in claim 1, in which the monitor comprises a number of electrodes that are configured to be placed in a non-invasive manner into operative engagement with the patient's head, such that at least one electrode engages each of a number of respective segments of the patient's head.

3. The system as claimed in claim 1, in which the monitor is configured to record steady state resistance on at least one frequency as well as pulsing wave resistance on at least one different frequency.

4. The system as claimed in claim 3, in which the monitor is configured to use at least three different frequencies between 16 and 400 kHz.

5. The system as claimed in claim 4, in which the monitor operates to capture impedance data on at least three different frequencies simultaneously.

6. The system as claimed in claim 4, in which the monitor is electronically switched automatically between the at least three frequencies at an adjustable rate to capture impedance data on at least three different frequencies.

7. The system as claimed in claim 1, in which the impedance data includes capacitance and resistance for different tissue structures.

8. The system as claimed in claim 1, in which the system is configured to store data in the form of impedance parameters, signal waveform segments, computed tabled data, raw data, graphed data and provide cumulative analysis using a database with extended functionality designed for the purpose of grouping and displaying anomalous tests when weighted against the database mean and averaged results of groups within said database.

9. The system as claimed in claim 1, in which the data output device is configured to output the plot in one or more of the following forms:
   a) near real-time;
   b) re-play of one or more previously recorded plots;
   c) mathematically reconstructed waveforms of one or more plots.

10. The system as claimed in claim 3, wherein the steady state resistance values are captured at a rate of 100 times per cardiac cycle.

11. The system as claimed in claim 1, wherein the non-invasive monitor separately monitors a left hemisphere and a right hemisphere of the patient's head.

12. The system as claimed in claim 4, wherein the at least three frequencies used are 16 Khz, 100 Khz and 200 Khz.

13. A method for measuring physiological characteristics, the method comprising the steps of:
   a. engaging at least one non-invasive monitors with a patient's head, the non-invasive monitor including a coupled transcranial Doppler and a multi-frequency rheoencephalograph, the monitor including at least one excitation electrode and at least one receiving electrode to be attached relative to the head and configured to generate at least one excitation charge on at least one frequency and introduce said at least one excitation charge to the patient's head, and monitor at least one resistive impedance signal on the rheoencephalograph and at least one Doppler signal on the transcranial Doppler, the at least one resistive impedance signal and the at least one Doppler signal being recorded simultaneously over time in a number of cardiac cycles;
   b. processing the at least one resistive impedance signal and the at least one Doppler signal in order to:
      i. synchronise the least one resistive impedance signal and the at least one Doppler signal by matching a minimum point of the at least one resistive impedance signal at a beginning of a given cardiac cycle with a minimum point of the at least one Doppler signal at the beginning of the given cardiac cycle;

ii. identify a systolic half and a diastolic half of the at least one resistive impedance signal and the at least one Doppler signal for the given cardiac cycle;
iii. plot the at least one Doppler signal on an X axis against the at least one resistive impedance signal on the Y axis for the given cardiac cycle, scaling the at least one Doppler signal, and scaling proportionally the at least one resistive impedance signal to match the scaling of the at least one Doppler signal to give a single waveform;
iv. invert the diastolic half of the plot;
v. align the systolic half of the plotted single waveform on a left side and the inverted diastolic half of the plotted single waveform on the right side to give a plot of a volume-pressure relation in the head for the given cardiac cycle; and
c. outputting the plot of the volume-pressure relation in the head for the given cardiac cycle.

14. The method as claimed in claim 13, in which the step of engaging the at least one non-invasive monitors with the patient's head includes the step of engaging an electrode montage with the patient's head such that at least two of several segments of the patient's head are monitored.

15. The method as claimed in claim 13, in which the plot is outputted in at least one of the following forms:
   a) near real-time;
   b) a re-play of one or more previously recorded plots;
   c) in combination with mathematically reconstructed waveforms of one or more plots.

* * * * *

UNITED STATES PATENT AND TRADEMARK OFFICE
CERTIFICATE OF CORRECTION

PATENT NO. : 10,201,304 B2
APPLICATION NO. : 14/776809
DATED : February 12, 2019
INVENTOR(S) : Terence Vardy It is certified that error appears in the above-identified patent and that said Letters Patent is hereby corrected as shown below:

In the Specification

Figure 21:
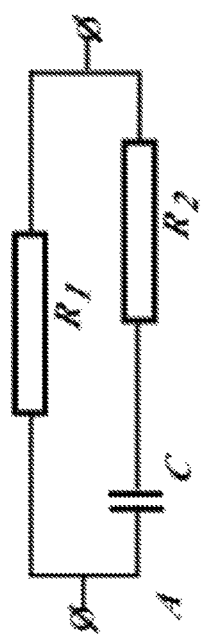
FIG. 21 is a schematic illustration of an equivalent electrical circuit of the human brain according to one author.
Figure 22:
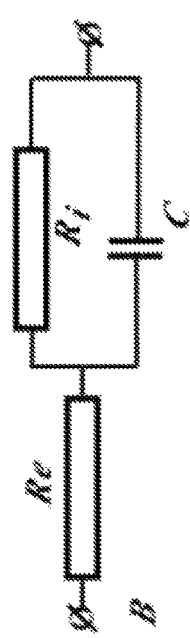
FIG. 22 is a schematic illustration of an equivalent electrical circuit of the human brain according to a second author.

Column 2, Line 58:
"FIGS. 26 and 27" should read "FIGS. 21 and 22";

Columns 2-3, Line 59, Line 60:
"FIG. 26" should read "FIG. 21";

Column 3, Line 40:
"FIG. 32" should read "FIG. 21" and "FIG. 27" should read "FIG. 22";

In the Claims

Column 18, Claim 13, Line 46:
"monitors" should read "monitor";

Column 19, Claim 14, Line 20:
"monitors" should read "monitor".

Signed and Sealed this
Twelfth Day of November, 2019

Andrei Iancu
*Director of the United States Patent and Trademark Office*